United States Patent
Kain et al.

(10) Patent No.: US 11,574,712 B2
(45) Date of Patent: Feb. 7, 2023

(54) ORIGIN PROTECTED OMIC DATA AGGREGATION PLATFORM

(71) Applicant: LunaPBC, Solana Beach, CA (US)

(72) Inventors: Robert C. Kain, San Diego, CA (US); Dawn Mary Barry, Solana Beach, CA (US); David Lewis, San Diego, CA (US); Kenneth Robert Bloom, San Diego, CA (US); Scott Kahn, Rancho Santa Fe, CA (US); Bojil Velinov, San Diego, CA (US)

(73) Assignee: LunaPBC, Solana Beach, CA (US)

( * ) Notice: Subject to any disclaimer, the term of this patent is extended or adjusted under 35 U.S.C. 154(b) by 237 days.

(21) Appl. No.: 16/377,922

(22) Filed: Apr. 8, 2019

(65) Prior Publication Data

US 2020/0035340 A1     Jan. 30, 2020

Related U.S. Application Data

(63) Continuation of application No. 16/192,341, filed on Nov. 15, 2018, now abandoned.
(Continued)

(51) Int. Cl.
*G16H 10/60* (2018.01)
*G16H 10/20* (2018.01)
(Continued)

(52) U.S. Cl.
CPC ......... *G16H 10/60* (2018.01); *G06F 16/2379* (2019.01); *G06F 16/958* (2019.01);
(Continued)

(58) Field of Classification Search
CPC .................................................. G16H 10/60
See application file for complete search history.

(56) References Cited

U.S. PATENT DOCUMENTS 5,974,409 A    10/1999   Sanu et al.
6,208,991 B1    3/2001   French et al.
(Continued)

FOREIGN PATENT DOCUMENTS

WO    2014/042942 A1    3/2014
WO    2015/123540 A1    8/2015
(Continued)

OTHER PUBLICATIONS

Bovenberg, Jasper A; "One Sample, One Share! A Proposal to Redress an Inequity with Equity;" Biobanks and Tissue Research. The Public, the Patient and the Regulation; Jan. 2011; 16 pages.
(Continued)

*Primary Examiner* — John A Pauls
(74) *Attorney, Agent, or Firm* — Fletcher Yoder P.C.

(57) ABSTRACT

A system and method are disclosed for the collection and aggregation of genomic, medical, and other data of interest for individuals and populations that may be of interest for analysis, research, pharmaceutical development, medical treatment, and so forth. Contributors become members of a community upon creation of an account and providing of data or files. The data is received and processed, such as to analyze, structure, perform quality control, and curate the data. Value or shares in one or more community databases are computed and attributed to each contributing member. The data is controlled to avoid identification or personalization. Third parties interested in the database information may contribute value (e.g., pay) for access and use. Value flows back to the members and to a system administrative entity.

19 Claims, 13 Drawing Sheets

Related U.S. Application Data

(60) Provisional application No. 62/712,063, filed on Jul. 30, 2018.

(51) Int. Cl.
    *G06F 16/23*     (2019.01)
    *G06F 16/958*     (2019.01)
    *G06N 20/00*     (2019.01)
    *G06Q 40/08*     (2012.01)

(52) U.S. Cl.
    CPC ............. *G06N 20/00* (2019.01); *G16H 10/20* (2018.01); *G06Q 40/08* (2013.01)

(56) References Cited

U.S. PATENT DOCUMENTS

| | | |
|---|---|---|
| 7,181,375 B2 | 2/2007 | Rao et al. |
| 7,306,562 B1 | 12/2007 | Baykal |
| 8,589,437 B1 | 11/2013 | Khomenko et al. |
| 8,589,589 B2 | 11/2013 | Clemm et al. |
| 9,110,553 B2 | 8/2015 | Ash et al. |
| 9,489,656 B2 | 11/2016 | Yoo et al. |
| 9,536,052 B2 | 1/2017 | Amarasingham et al. |
| 10,025,877 B2 | 7/2018 | Macpherson |
| 10,162,880 B1 | 12/2018 | Chowdry et al. |
| 10,172,517 B2 | 1/2019 | Jain et al. |
| 2002/0052761 A1* | 5/2002 | Fey .................. G16H 50/30 705/2 |
| 2002/0095585 A1* | 7/2002 | Scott ............... G06Q 10/10 713/185 |
| 2003/0040002 A1 | 2/2003 | Ley |
| 2004/0034550 A1 | 2/2004 | Menschik et al. |
| 2005/0010435 A1 | 1/2005 | Kato et al. |
| 2005/0108551 A1 | 5/2005 | Toomey |
| 2005/0119534 A1 | 6/2005 | Trost et al. |
| 2005/0132104 A1 | 6/2005 | Brown |
| 2005/0158767 A1* | 7/2005 | Haskell .............. G06Q 50/24 435/6.11 |
| 2006/0085454 A1* | 4/2006 | Blegen ............... G06F 21/6254 |
| 2006/0129427 A1 | 6/2006 | Wennberg |
| 2006/0173663 A1 | 8/2006 | Langheier et al. |
| 2007/0055552 A1 | 3/2007 | St. Clair et al. |
| 2007/0136378 A1 | 6/2007 | Karpf et al. |
| 2007/0258902 A1 | 11/2007 | Hwang et al. |
| 2007/0276768 A1 | 11/2007 | Pallante |
| 2008/0081331 A1 | 4/2008 | Myres et al. |
| 2008/0120296 A1 | 5/2008 | Kariathungal et al. |
| 2008/0131887 A1 | 6/2008 | Stephan et al. |
| 2008/0177799 A1 | 7/2008 | Wilson |
| 2008/0222299 A1 | 9/2008 | Boodaei |
| 2008/0313262 A1 | 12/2008 | Cho et al. |
| 2009/0055217 A1 | 2/2009 | Grichnik et al. |
| 2009/0132282 A1 | 5/2009 | Kerstna et al. |
| 2010/0047803 A1* | 2/2010 | Weinshilboum ..... C12Q 1/6883 435/6.16 |
| 2010/0145953 A1 | 6/2010 | Charles et al. |
| 2010/0249531 A1 | 9/2010 | Hanlon et al. |
| 2010/0316251 A1 | 12/2010 | Cowburn et al. |
| 2010/0331146 A1 | 12/2010 | Kil |
| 2013/0185421 A1 | 7/2013 | Orr et al. |
| 2014/0012843 A1 | 1/2014 | Soon-Shiong |
| 2014/0046680 A1 | 2/2014 | Wentz et al. |
| 2014/0058844 A1* | 2/2014 | Jadeja ................ G06Q 30/0269 705/14.66 |
| 2014/0095201 A1 | 4/2014 | Farooq et al. |
| 2014/0164003 A1 | 6/2014 | Thesman |
| 2014/0222966 A1 | 8/2014 | Marins et al. |
| 2014/0229495 A1 | 8/2014 | Makkapati et al. |
| 2014/0324466 A1 | 10/2014 | Wertzberger |
| 2015/0074760 A1 | 3/2015 | Yan et al. |
| 2015/0205929 A1 | 7/2015 | Brama |
| 2015/0235006 A1 | 8/2015 | Nichols |
| 2015/0244690 A1 | 8/2015 | Mossbarger |
| 2015/0294069 A1 | 10/2015 | Shah |
| 2015/0332283 A1 | 11/2015 | Witchey |
| 2015/0379510 A1 | 12/2015 | Smith |
| 2016/0055236 A1 | 2/2016 | Frank et al. |
| 2016/0210692 A1 | 6/2016 | Perez |
| 2017/0140477 A1 | 5/2017 | Heywood et al. |
| 2017/0329904 A1 | 11/2017 | Naughton et al. |
| 2017/0330174 A1* | 11/2017 | Demarinis ............. G06Q 40/04 |
| 2018/0039737 A1 | 2/2018 | Dempers et al. |
| 2018/0294047 A1 | 10/2018 | Hosseini et al. |
| 2018/0294048 A1 | 10/2018 | Blumenthal et al. |
| 2018/0307859 A1 | 10/2018 | LaFever et al. |
| 2018/0330824 A1 | 11/2018 | Athey et al. |
| 2018/0341648 A1 | 11/2018 | Kakavand et al. |
| 2018/0368819 A1 | 12/2018 | Gogineni |
| 2019/0006048 A1 | 1/2019 | Gupta et al. |
| 2019/0020651 A1 | 1/2019 | Soon-Shiong et al. |
| 2019/0026425 A1 | 1/2019 | Downs et al. |

FOREIGN PATENT DOCUMENTS

| | | |
|---|---|---|
| WO | 2015/157572 A1 | 10/2015 |
| WO | 2015/171580 A1 | 11/2015 |
| WO | 2016/005793 A1 | 1/2016 |
| WO | 2016/077727 A1 | 5/2016 |
| WO | 2016/189488 A2 | 12/2016 |
| WO | 2017/136643 A1 | 8/2017 |
| WO | 2017/146363 A1 | 8/2017 |
| WO | 2017/209446 A1 | 12/2017 |
| WO | 2018/177663 A1 | 10/2018 |
| WO | 2018/177664 A1 | 10/2018 |

OTHER PUBLICATIONS

International Search Report and Written Opinion for PCT/US2018/067933 dated Sep. 18, 2019; 15 pages.
International Search Report and Written Opinion for PCT/US2018/061419 dated Feb. 25, 2019, 14 pages.
Examination Report for Australian Application No. 2018370131 dated May 26, 2021, 6 pages.

\* cited by examiner

SHARE TABLE

| DATA TYPE | SHARES PER INITIAL FILE | EXTRA SUBMISSIONS* ALLOWED AT INITIAL FILE VALUE | SUBTOTAL SHARES AT INITIAL FILE VALUE | ADDITIONAL FILES** OF SAME TYPE ALLOWED (@ 10 SHARES EACH) | SUBTOTAL ADDITIONAL SHARES (@ 10 SHARES EACH) | MAX POSSIBLE SHARES |
|---|---|---|---|---|---|---|
| DNA TARGETED GENE DATA | 10 | -- | 10 | 4 | 40 | 50 |
| DNA GENOME-WIDE MICROARRAY | 50 | -- | 50 | 2 | 20 | 70 |
| DNA EXOME | 150 | -- | 150 | 3 | 30 | 180 |
| DNA WHOLE GENOME SEQUENCE | 200 | -- | 200 | 2 | 20 | 220 |
| DNA TUMOR TARGETED PANEL | 10 | 4 TIME POINTS/YEAR | 40 | 3 | 120 | 160/YEAR |
| DNA TUMOR MICROARRAY | 50 | 4 TIME POINTS/YEAR | 200 | 3 | 120 | 320/YEAR |
| DNA TUMOR EXOME | 150 | 4 TIME POINTS/YEAR | 600 | 3 | 120 | 720/YEAR |
| DNA TUMOR WHOLE GENOME SEQUENCE | 200 | 4 TIME POINTS/YEAR | 800 | 3 | 120 | 920/YEAR |
| DNA EPIGENOME PANEL + SURVEY | 10 | -- | 10 | 0 | 0 | 10 |
| DNA WHOLE EPIGENOME + SURVEY | 20 | -- | 20 | 0 | 0 | 20 |
| RNA GENOME-WIDE MICROARRAY + SURVEY | 10 | 4 TISSUES/YEAR | 40 | 0 | 0 | 40/YEAR |
| RNA GENE PANEL + SURVEY | 20 | 4 TISSUES/YEAR | 80 | 0 | 0 | 80/YEAR |
| RNA WHOLE TRANSCRIPTOME + SURVEY | 40 | 4 TIME POINTS/YEAR | 160 | 0 | 0 | 160/YEAR |
| RNA TUMOR MICROARRAY | 10 | 4 TIME POINTS/YEAR | 40 | 3 | 120 | 160/YEAR |
| RNA TUMOR TARGETED GENE PANEL | 20 | 4 TIME POINTS/YEAR | 80 | 3 | 120 | 200/YEAR |
| RNA TUMOR WHOLE TRANSCRIPTOME | 40 | 4 TIME POINTS/YEAR | 160 | 3 | 120 | 280/YEAR |
| TARGETED MICROBIOME + SURVEY | 10 | 4 REGIONS/YEAR | 40 | 0 | 0 | 40/YEAR |
| WHOLE MICROBIOME + SURVEY | 20 | 4 REGIONS/YEAR | 80 | 0 | 0 | 80/YEAR |
| DIGITAL HEALTH RECORD (PER MONTH OF REPORTS) | 5 | 12 MONTHS/YEAR | 60 | 0 | 0 | 60/YEAR |
| PDF OF HEALTH RECORD (PER YEAR OF REPORTS) | 2 | -- | 2 | 0 | 0 | 2 |
| ELECTRONIC SURVEY (PER 10MIN TO COMPLETE) | 2 | UPDATES 1X/YEAR | DEP. ON # SURVEYS | | | |
| PERSONAL FITNESS MONITOR (PER MONTHS OF DATA) | 2 | 12 MONTHS/YEAR | 24 | 0 | 0 | 24/YEAR |
| CLINICALLY CERTIFIED DEVICE (PER MONTH OF DATA) | 10 | 12 MONTHS/YEAR | 120 | 0 | 0 | 120/YEAR |
| NUTRITION TRACKER (PER MONTH OF DATA) | 2 | 12 MONTHS/YEAR | 24 | 0 | 0 | 24/YEAR |

FIG. 8

ORIGIN PROTECTED OMIC DATA AGGREGATION PLATFORM

CROSS-REFERENCE TO RELATED APPLICATIONS

This application claims priority from and the benefit of U.S. Provisional Application Ser. No. 62/712,063, entitled "Genomic and Medical Data Aggregation System and Method," filed Jul. 30, 2018; U.S. Provisional Application Ser. No. 62/647,572, entitled "OMIC Information Database and Management Systems," filed Mar. 23, 2018; and U.S. Provisional Application Ser. No. 62/587,842, entitled "OMIC Information Database and Management Systems," filed Nov. 17, 2017, all of which are hereby incorporated by reference in their entirety.

BACKGROUND

The invention relates generally to the aggregation of personal data, which may include omic and phenotype data. In particular, the techniques disclosed provide for aggregating contributed data from members of a community who share value by virtue of their contribution and consenting to the use of their aggregated data.

In the present context, personal, omic, genomic, medical, health, environmental, demographic, and other data, and more generally any and all data relating to physical states of organisms may be contributed by members of a community to one or more databases where the data may be processed, and other data may be derived from it, and ultimately aggregated with data from other contributing members. The aggregated data is then made available for research and other activities that might benefit from it, while reducing barriers to sharing of the data, and enhancing benefits to data contributors. Broad and comprehensive non-genomic data (e.g., phenotype data) is sometime referred to as "real world data" when looking at discoveries that improve health and quality of life. Real world data (RWD) in medicine may be data derived from a number of sources that are associated with outcomes in a heterogeneous patient population in real-world settings, such as patient surveys, clinical trials, and observational cohort studies. Real world data may refer to observational data as opposed to data gathered in an experimental setting such as a randomized controlled trial (RCT). They are derived from electronic health records (EHRs), claims and billing activities, product and disease registries, etc. During recent years, genome-wide association studies (GWAS) have emerged as a primary method of discovering genetic variants associated with complex traits and disease. Unlike traditional linkage mapping approaches, which are based on analyzing patterns of disease inheritance in families, GWAS is based on the observation that genetic markers that are close to a causative disease allele are often statistically associated with disease status in large cohorts of unrelated individuals. A major strength of GWAS is its ability to locate causative genetic variants with fine-scale resolution when the markers are single nucleotide polymorphisms, single base insertions, or single base deletions. However, when evaluating complex traits or disease associations, GWAS requires obtaining and analyzing data from large numbers of samples. Additionally GWAS data does not comprehensively cover the human genome, and cover all varieties of genomic structural variation, and so it may not be sufficient to identify the genomic association. In many cases, data from tens of thousands of individuals are required to achieve adequate statistical power. In other case fulle exome sequencing or full genome sequencing may be required to identify an association. In the future more comprehensive or complete genomic and o'mic data will be generated through whole genome sequencing, pathogen sequencing, epigenome sequencing, metabolome analysis, and microbiome sequencing.

Currently a large amount of data is freely available from public databases such as the National Center for Biotechnology Information (NCBI). However, in general such data have been of little interest to the pharmaceutical industry because of high variation in data quality, standards of data encoding, and information gaps in the data such as corresponding phenotypic information. To meet these criteria, pharmaceutical companies typically rely on data collected in-house.

Much of the genomic data and phenotype data collected by pharmaceutical companies remains "siloed", inaccessible to the research community at large. In some cases, the reason is inefficient database design, need to maintain a proprietary advantage over competitive entities, or poor data management practices. The pharmaceutical industry lags behind other sectors in several indicators of digital maturity. Nevertheless, many pharmaceutical companies have begun integrating patient data from applications, wearable devices, and electronic medical records to improve healthcare and make discoveries about disease. Recently, technology companies have also entered this market. Given these trends, it seems unlikely that the pace of future research will be limited by information technology problems.

A more serious problem is that many pharmaceutical and biotech companies forgo an open, collaborative approach to research and development for understandable strategic reasons, for instance because they estimate its financial or discovery benefits are outweighed by legal, regulatory, and intellectual property risks. As a consequence, public trust in their research efforts is eroded by a lack of transparency and sense of common purpose, and a distrust of the companies ultimate motives, which discourages study participants from providing broad consent to use their data. Decisions on how broadly consented data may be used in secondary studies after a primary study is completed are made independently at various institutions by ad-hoc data access committees (DACs) and institutional review boards (IRBs), and tend to be arbitrary and inconsistent. Often the ability to recontact the study participant is lost, resulting in an inability to collect valuable and/or necessary additional data. In practical terms, this variability means the usefulness of a collection of data sets is circumscribed by the subset with the narrowest terms of consent and the narrow nature of the original collected data. This presents a clear scalability problem.

If consent is narrow on the other hand, the consent may be suitable for pharmaceutical companies interested in deep, focused studies of a particular biological function or disease. However, narrow consent is unsuitable for the broad exploratory studies that are a critical counterpart to these more focused efforts.

Privacy concerns are a major factor in the design of any biomedical study involving human participants. These concerns arise from the many potential abuses of personal genetic and medical data, including denial of healthcare services due to genetic predispositions, racial discrimination, and disclosure intimate familial relationships such as non-paternity. In current practice, privacy is typically protected by concealing the identities of study participants, while de-identified data is shared freely. Standard data security controls are sufficient for protecting identity data itself, but in many cases the freely-shared component remains vulnerable to misuse. For example, advances in re-identification techniques have made it possible to infer surnames from certain types of genetic data and to identify relatives from data in public databases.

A trusting relationship between researchers and study participants involves a component of privacy and transparency, in addition to other factors. There are a variety of reasons people participate in biomedical studies. Some reasons may be personal, such as the desire to know one's ancestry and disease predispositions. Other motivations may be broader, such as the desire to improve human health and society. Participants are most likely to give broad consent to use their data when all parties involved in the research trust each other, respect one another's goals, control of data is maintained, and usage of the data is communicated.

There is a keen and ongoing need, therefore, for improved approaches to the aggregation of medical-related, and particularly of genetic and similar data that would enhance the opportunities for research and discovery that could benefit all of mankind, while allowing confidentiality and trust between individuals providing data and users of the data, and that, moreover, would create a "win-win" relationship in the provision and use of such data.

While particularly promising benefits may be drawn from aggregation of what may be termed "medical" data, increasingly, issues and concerns continue to surface regarding the use and control of personal data in a more general sense. That is, social media, marketing, commercial, pharmaceutical, and other platforms allow and even encourage individuals to share vast amounts of personal information, some of it extremely personal and sensitive. While legislation and regulation have not kept pace with such technologies, anyone who is "connected" to in any meaningful way to digital media may be surprised to learn about the scope and scale of amounts of data that is collected, stored, and analyzed about them and relevant groups, communities, and cohorts to which they may, knowingly or unknowingly belong. Such data may include personal life details, demographic data, family details, purchases, interests and web activities, occupational and social organization data, health data, movements and whereabouts, and much more. In general, individuals are provided little or no notice of just what information is collected (and shared by others), and even less are they offered ownership, control, or benefits from the use of the data. Additionally many such consents, which people have no choice but to accept, in order to utilize online services, grant the provider broad rights to utilize and share the data as they see fit, with little or no notice to the data providers.

Such "personal data", if considered as owned by the individual, takes on a precious aspect that can and should be subject to more control by each person to whom it relates. But when considered in the context of the social, societal, or monetary benefits that could accrue and flow from its being shared, aggregated, and made available in meaningful ways and in which the contributor actually owns or receives actual value from one or more aggregated databases, its power may be multiplied manyfold. And when considered in combination with medical or health data of the type discussed above, possibilities for benefitting both the contributing individuals and society are enormous. But, if considered owned by the individual, such sharing should always respect the desires and sensitivities of the contributors.

BRIEF DESCRIPTION

The underlying premise behind the present inventions is that a community ownership plan creates a people-driven scientific enterprise perceived as one worth joining, and based upon the premise that the best way to encourage new contributors to join and broadly consent to the use of their data is to make them full and engaged partners in the project. This may imply databases that will be 100% owned, or partially owned by data contributors, who will gain increased stakes as they contribute genomic data, phenotype data, health, and other personal data of interest. Unlike other approaches in the field, proceeds generated by providing access to the data (for instance to pharmaceutical companies) will be apportioned among the community based on for instance total and types of contributions to the community. Furthermore in order to provide contributors control over their data, contributors will have the ability to withdraw consent by returning their original stake or a stake of commensurate value at any point.

Aside from a formal stake in the enterprise (sometimes referred to in the present disclosure as "the system"), partnership may also mean seeing the studies and the results of such studies that are performed, and having the opportunity to provide feedback on what is happening with the database. For many participants, a primary motivation will be to support the greater good through scientific discovery. The system or the system administrator or sponsor may aim to encourage this type of participation through regular communications to build trust in the management of the database, and its contributions to science.

Community ownership solves many of the problems of trust and data control that act as obstacles to participation in biomedical studies, but for it to be effective the mechanism of ownership cannot itself become an obstacle. Encrypted databases, cryptographic ledgers, such as cryptocurrency coins and similar devices may provide a straightforward and hassle-free means to implement decentralized and large scale ownership. After making their initial data contribution, participants may earn additional participation, ownership, coins, etc. (sometimes collectively referred to in the present disclosure as "value") for contributing additional data.

A primary goal may be to identify the molecular basis of disease, causes of a chronic disease, or social determinants of disease, even if the economics are insufficient for commercial organizations to underwrite the efforts. In such cases the system could partner with nonprofit organizations or the National Institutes of Health (NIH) at cost or pro bono. Nevertheless, the focus may often be on use-inspired basic research (sometimes referred to as Pasteur's Quadrant in the spectrum of activities ranging from applied to basic research).

One long term goal may be increasing the value of the "coins" or "value" attributed to data contributors (sometimes referred to in the present disclosure as "members") by maximizing the value of the database. This goal will incentivize members or collaborators to partner will all players in the ecosystem even at the expense of short term profits (e.g., partner of choice in the full ecosystem). It will also align goals with those of the member community (i.e., focus on the intrinsic benefits and intangible satisfaction of solving life's most important problems).

In some embodiments, new data contributors may receive a digital "wallet ID" and a custom cryptocurrency coin, that is designed to represent or track the value of the database asset, every time they contribute additional data. A wide range of genomic and omic data types may be accepted, including for example SNP array data, DNA sequencing data, somatic genome data, methylome data, virome data, pathegenomic data, and microbiome data. High-quality health, medical, and environmental data may also be accepted, including electronic medical records, surveys on diet and exercise, health history, and data from wearable devices, and personal and/or demographic data that might prove insightful for research. Environmental data may also be accepted such as water quality, weather, air quality, and other data relating to an individual's exposome. The exposome can be defined as the measure of all the exposures of an individual in a lifetime and how those exposures relate to health. The database(s) may also accept data pertaining to non-human subjects and organisms, including animals, plants, microbes, viruses, fungi, or even "environmental" data such as to determine all possible organisms present.

In certain disclosed embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; a centralized database maintained by an administrative entity that, in operation, stores and aggregates the member-specific contributed data with member-specific contributed data contributed by other contributing members; and processing circuitry maintained by the administrative entity that, in operation, processes member-specific account data received from the contributing members via the interface pages to establish member-specific accounts based on the member-specific account data, and attributes a member-specific value to the member-specific accounts based upon respective member-specific contributed data.

In certain of these embodiments, the processing circuitry attributes the member-specific value based upon a pre-established calculation applied to all contributing members, and/or the processing circuitry transfers an asset amount to each member-specific account as consideration for member-specific contributed data of the respective contributing member, and/or the asset amount is calculated by a formula having a generalized form:

$$F = x/y;$$

wherein F is the fraction of ownership; x is the sum of $((W1) \times (\text{sum of data units of a first type of data unit}) + (W2) \times (\text{sum of data units of a second type of data unit}) + (W3) \times (\text{sum of data units of a third type of data unit}) \ldots + (Wn) \times (\text{sum of data units of an n type of data unit}))$ associated with the account; y is the sum of $((W1) \times (\text{sum of data units of the first type of data unit}) + (W2) \times (\text{sum of data units of the second type of data unit}) + (W3) \times (\text{sum of data units of the third type of data unit}) \ldots + (Wn) \times (\text{sum of data units of the n type of data unit}))$ associated with all accounts; and $W1, W2, W3 \ldots Wn$ are optional weighting factors, and/or the database is configured to store member-specific contributed data of different types, and the processing circuitry attributes the member-specific value based upon types of member-specific contributed data submitted by each member, and/or the types of member-specific contributed data comprise at least omic and phenotype data, and also at least one of health data, personal data, familial data and environmental data, and/or the omic data comprises one or more of genomic data, microbiomic data, epigenomic data, transcriptomic data and proteomic data, and/or the genomic data comprises one or more of genotype data, single nucleotide polymorphism data, short tandem repeat data, microsatellite data, haplotype data, epigenomic data, genome methylation data, microbiomic data, whole or partial gene sequence data, whole or partial exome sequence data, whole or partial chromosome data, and whole or partial genome sequence data, and/or the health data comprises one or more of medical record data, exercise data, dietary data and wearable device data, and/or the database is configured to separately store member-specific contributed data for a respective member personally, an animal, plant, or microbial species owned or controlled by a respective member, and an environment owned or controlled by a respective member, and/or the user-specific value is attributed as a currency and/or a cryptocurrency and/or an ownership share in the database, and/or the contributed data undergoes a quality analysis and a value and/or store indicative of the quality analysis is stored, and/or the quality analysis is tuned by artificial intelligence and/or machine learning, and/or the database comprises an immutable and/or cryptographically encoded ledger and/or a blockchain.

In other embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; a database that, in operation, stores and aggregates the member-specific contributed data with member-specific contributed data contributed by other contributing members; and processing circuitry that, in operation, processes member-specific account data received from the contributing members via the interface pages to establish member-specific accounts based on the member-specific account data, and attributes a member-specific value to the member-specific accounts based upon respective member-specific contributed data; wherein the processing circuitry attributes the member-specific value based upon a pre-established calculation applied to all contributing members; and wherein the processing circuitry transfers an asset amount to each member-specific account as consideration for the member-specific contributed data of the respective contributing member.

In certain of these embodiments, the database comprises an immutable and/or cryptographically encoded ledger, and/or the immutable ledger comprises a blockchain. Other features such as those summarized above may also be combined in these embodiments.

In other embodiments, a computer-implemented method comprises serving interface pages from a server to contributing members of an aggregation community; receiving, from the contributing members, member-specific account data and member-specific contributed data, the member-specific contributed data comprising omic and/or phenotype data submitted by each contributing member or data derived therefrom; storing, in a database, the member-specific contributed data; aggregating the member-specific contributed data with member-specific contributed data of other contributing members; establishing a member-specific account for each contributing member based on the member-specific account data; and attributing a member-specific value to each member-specific account based upon member-specific contributed data of the respective contributing member, and/or the member-specific value is attributed based upon a pre-established calculation applied to all contributing members, and an asset amount is transferred to each member-specific account as consideration for member-specific contributed data submitted by each member or for data derived therefrom, and/or the database comprises a secure, immutable, and/or cryptographically encoded ledger and/or a blockchain. Other features such as those summarized above may also be combined in these embodiments.

In still further embodiments, a system comprises a server that, in operation, serves interface pages to contributing members of an aggregation community for receipt of member-specific account data and member-specific contributed data, the member-specific contributed data comprising personal data submitted by each contributing member or data derived therefrom; a centralized database maintained by an administrative entity that, in operation, stores and aggregates the member-specific contributed data with member-specific contributed data contributed by other contributing members; and processing circuitry maintained by the administrative entity that, in operation, processes member-specific account data received from the contributing members via the interface pages to establish member-specific accounts based on the member-specific account data, and attributes a member-specific value to the member-specific accounts based upon respective member-specific contributed data.

In certain of these embodiments, the contributed data undergoes a quality analysis and a value and/or score indicative of the quality analysis is stored, and/or the quality analysis is tuned by artificial intelligence and/or machine learning, and/or the personal data comprises at least omic and/or phenotype data for the respective contributing member, and/or the types of member-specific contributed data comprises at least one of medical data, health data, personal data, exposome data, pathogen data, virome data, familial data and environmental data, and/or the database is configured to store member-specific contributed data of different types, and the processing circuitry attributes the member-specific value based upon types of member-specific contributed data submitted by each member, and/or the member-specific value comprises partial ownership interest in the database, and/or the member-specific value comprises a cryptocurrency, and/or an immutable ledger records transactions including submission of member-specific contributed data and attribution of member-specific value, and/or the processing circuitry attributes the member-specific value based upon a pre-established calculation applied to all contributing members, and/or the processing circuitry transfers an asset amount to each member-specific account as consideration for member-specific contributed data of the respective contributing member, and/or the asset amount is calculated by a formula having a generalized form:

$$F=x/y;$$

wherein F is the fraction of ownership; x is the sum of $((W1) \times (\text{sum of data units of a first type of data unit}) + (W2) \times (\text{sum of data units of a second type of data unit}) + (W3) \times (\text{sum of data units of a third type of data unit}) \ldots + (Wn) \times (\text{sum of data units of an n type of data unit}))$ associated with the account; y is the sum of $((W1) \times (\text{sum of data units of the first type of data unit}) + (W2) \times (\text{sum of data units of the second type of data unit}) + (W3) \times (\text{sum of data units of the third type of data unit}) \ldots + (Wn) \times (\text{sum of data units of the n type of data unit}))$ associated with all accounts; and $W1$, $W2$, $W3 \ldots Wn$ are optional weighting factors. Other features such as those summarized above may also be combined in these embodiments.

In certain embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; processing circuitry that, in operation, interacts with data received via the server; an account database that, in operation, cooperates with the processing circuitry to receive and store member-specific account data based upon interaction of a contributing members; and a second database that, in operation, cooperates with the processing circuitry to receive and store member-specific contributed data submitted by each member, and aggregates the member-specific contributed data with member-specific contributed data contributed by other contributing members; wherein the stored and aggregated member-specific contributed data is de-identified from the stored member-specific account data.

In some of these embodiments, the member-specific account data is received and stored in accordance with an account blockchain or distributed ledger protocol, and/or the member-specific contributed data is received and stored in accordance with a contributed data blockchain or distributed ledger protocol, and/or as the member-specific contributed data is received and stored ledger entries are made separately to an account blockchain or distributed ledger and to a contributed data blockchain or distributed ledger, and/or the processing circuitry invokes a universal resource identifier protocol to process the member-specific contributed data, and/or each member-specific account is associated with a data key, and/or the data key for each member-specific account is stored in an encrypted manner on a blockchain with a one-way pointer from personal information indicative of the member-specific account to the respective data key, and/or the second database stores member-specific contributed data of different types, including at least omic data and health data, and wherein at least two data types are associated with a different respective data keys, and/or the second database is maintained by an administrative entity that allows analysis of the aggregated member-specific contributed data, and wherein the administrative entity does not link member-specific contributed data to an associated member-specific account in a manner that would personally identify the respective contributing member without permission of the respective contributing member, and/or separate portals are provided for receiving the member-specific account data and the member-specific contributed data, and/or the account database comprises a centralized database maintained by an administrative entity and the processing circuitry is maintained by the administrative entity, and/or the second database comprises a centralized database maintained by an administrative entity and the processing circuitry is maintained by the administrative entity.

In other embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; processing circuitry that, in operation, interacts with data received via the server; an account database that, in operation, cooperates with the processing circuitry to receive and store member-specific account data based upon interaction of a contributing members; and a second database that, in operation, cooperates with the processing circuitry to receive and store member-specific contributed data submitted by each member, and aggregates the member-specific contributed data with member-specific contributed data contributed by other contributing members, wherein the stored and aggregated member-specific contributed data is de-identified from the stored member-specific account data; and a portal that permits interaction by the contributing members with the server to access the respective member-specific account data via an account identification feature; wherein the portal is configured to permit access to the respective member-specific account data for a respective contributing member by a requestor via a secure alternative authentication protocol that maintains a de-identified nature of the stored member-specific contributed data of the respective contributing member.

In some of these embodiments, the account identification feature comprises a user name and password, and/or the requestor comprises the respective member or a successor in interest to the respective member, and/or the secure alternative authentication protocol comprises receipt of data indicative of at least a portion of the respective member-specific contributed data, and/or the secure alternative authentication protocol comprises interaction with at least one data key associated with the respective member-specific account data, and/or a portal permits interaction by the contributing members with the server to access the respective member-specific contributed data, and/or the secure alternative authentication protocol permits access to the respective member-specific contributed data, and/or the processing circuitry is configured to attribute a member-specific value to each member-specific account based upon member-specific contributed data of the respective contributing member, and wherein the identification feature and the secure alternative authentication protocol permit access to data indicative of the member-specific value, and/or the secure alternative authentication protocol comprises accessing a contact address for the respective contributing member, and sending data to the contact address without accessing the stored member-specific contributed data of the respective contributing member, and/or the second database is maintained by an administrative entity that is precluded from access the member-specific contributed data either via the identification feature or the secure alternative authentication protocol, and/or the account database comprises a centralized database maintained by an administrative entity and the processing circuitry is maintained by the administrative entity, and/or the second database comprises a centralized database maintained by an administrative entity and the processing circuitry is maintained by the administrative entity.

In still other embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; a database that, in operation, stores and aggregates the member-specific contributed data with member-specific contributed data contributed by other contributing members; and processing circuitry that, in operation, processes the received and stored member-specific contributed data and performs a quality evaluation of the received and stored member-specific contributed data.

In some of these embodiments, operations of the quality evaluation of the received and stored member-specific contributed data follow a blockchain or distributed ledger protocol, and/or the blockchain or distributed ledger protocol comprises ledger entries for results of operations in the quality evaluation of the received and stored member-specific contributed data, and/or the quality evaluation is performed on structured data or files derived from the received and stored member-specific contributed data, and/or the quality evaluation comprises analyzing the received and stored member-specific contributed data for redundancy with member-specific contributed data already provided by a contributing member, and/or the quality evaluation comprises analyzing the received and stored member-specific contributed data for inconsistency with member-specific contributed data already provided by a contributing member, and/or the quality evaluation comprises analyzing the received and stored member-specific contributed data by comparison of the data with reference data, and/or the comparison is performed for omic data, and the reference data comprises species-specific genomic reference data, and/or the server is configured to send a notice to a contributing member of results of the quality evaluation of the respective member-specific contributed data, and/or the processing circuitry is configured to generate a report of results of the quality evaluation of the respective member-specific contributed data, and/or an account database comprises a centralized database maintained by an administrative entity and the processing circuitry is maintained by the administrative entity, and/or the database comprises a centralized database maintained by an administrative entity and the processing circuitry is maintained by the administrative entity.

In still other embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; a database that, in operation, stores and aggregates the member-specific contributed data with member-specific contributed data contributed by other contributing members; and processing circuitry that, in operation, processes the received and stored member-specific contributed data and performs a contributor evaluation of the received and stored member-specific contributed data.

In some of these embodiments, the processing circuitry is configured to determine a contributor score based upon the contributor evaluation, and/or the processing circuitry is configured to attribute a member-specific value to a member-specific account for each contributing member based upon member-specific contributed data of the respective contributing member, and wherein the member-specific value is at least partially based upon the contributor evaluation, and/or the contributor evaluation comprises evaluation of past data submissions by the respective contributing member, and/or the contributor evaluation comprises evaluation of a third party source of the member-specific contributed data, and/or the contributor evaluation comprises identifying certain contributing members as trusted, and wherein processing of later member-specific contributed data is altered for trusted contributing members, and/or operations of the contributor evaluation of the received and stored member-specific contributed data follow a blockchain or distributed ledger protocol, and/or the blockchain or distributed ledger protocol comprises ledger entries for results of operations in the contributor evaluation of the received and stored member-specific contributed data, and/or the contributor evaluation is performed on structured data or files derived from the received and stored member-specific contributed data, and/or the server is configured to send a notice to a contributing member of results of the contributor evaluation of the respective member-specific contributed data, and/or an account database comprises a centralized database maintained by an administrative entity and the processing circuitry is maintained by the administrative entity, and/or the database comprises a centralized database maintained by an administrative entity and the processing circuitry is maintained by the administrative entity.

In still further embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; a database that, in operation, stores and aggregates the member-specific contributed data with member-specific contributed data contributed by other contributing members; and processing circuitry that, in operation, processes the received and stored member-specific contributed data and performs a quality evaluation comprising an evaluation of reliability or credibility of a contributing member and/or evaluation of quality of data submitted by the contributing member; wherein the processing circuitry is configured to attribute a member-specific value to a member-specific account for each contributing member based upon member-specific contributed data of the respective contributing member, and wherein the member-specific value is at least partially based upon the quality evaluation.

In certain of these embodiments, the processing circuitry attributes the member-specific value based upon a pre-established calculation applied to all contributing members and taking into account the quality evaluation of the member-specific contributed data for each contributing member, and/or the processing circuitry transfers an asset amount to each member-specific account as consideration for member-specific contributed data of the respective contributing member, the asset amount being based at least partially on the quality evaluation of the member-specific contributed data for the respective contributing member, and/or the operations in the quality evaluation of the received and stored member-specific contributed data follow a blockchain or distributed ledger protocol, and/or the blockchain or distributed ledger protocol comprises ledger entries for results of operations in the quality evaluation of the received and stored member-specific contributed data, and/or the quality evaluation is performed on structured data or files derived from the received and stored member-specific contributed data, and/or the quality evaluation comprises analyzing the received and stored member-specific contributed data for redundancy with member-specific contributed data already provided by a contributing member, and/or the quality evaluation comprises analyzing the received and stored member-specific contributed data for inconsistency with member-specific contributed data already provided by a contributing member, and/or the quality evaluation comprises analyzing the received and stored member-specific contributed data by comparison of the data with reference data, and/or the contributor evaluation comprises evaluation of past data submissions by the respective contributing member or evaluation of a third party source of the member-specific contributed data, and/or an account database comprises a centralized database maintained by an administrative entity and the processing circuitry is maintained by the administrative entity, and/or the database comprises a centralized database maintained by an administrative entity and the processing circuitry is maintained by the administrative entity.

In further embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; a database that, in operation, stores and aggregates the member-specific contributed data with member-specific contributed data contributed by other contributing members; and processing circuitry that, in operation, processes member-specific account data received from the contributing members via the interface pages to establish member-specific accounts based on the member-specific account data, and attributes a member-specific value to the member-specific accounts based upon respective member-specific contributed data; wherein the processing circuitry and the server cooperate to provide educational interface pages to contributing members for educating contributing members of issues with member-specific contributed data.

In some of these embodiments, the processing circuitry attributes the member-specific value based upon a pre-established calculation applied to all contributing members, and/or the member-specific value is altered based upon interaction of the respective contributing member with the educational interface pages, and/or alteration of the member-specific value is based upon a blockchain or distributed ledger protocol, and/or the blockchain or distributed ledger protocol comprises smart code and/or a smart contract, and/or the blockchain or distributed ledger protocol comprises ledger entries for stages of interaction by the respective contributing member with the educational interface pages, and/or the stages comprise completion of successive educational modules, and/or at least one of the educational interface pages provides a link to an educational video, and/or the processing circuitry is configured to compensate contributing members based upon interaction by the respective contributing member with the educational interface pages, and/or compensation of the contributing members based upon interaction with the educational interface pages comprises allocating a cryptocurrency to the member-specific account for the respective contributing member, and/or an account database comprises a centralized database maintained by an administrative entity and the processing circuitry is maintained by the administrative entity, and/or the database comprises a centralized database maintained by an administrative entity and the processing circuitry is maintained by the administrative entity.

In other embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; processing circuitry that, in operation, interacts with data received via the server; an account database that, in operation, cooperates with the processing circuitry to receive and store member-specific account data based upon interaction of a contributing members; a second database that, in operation, cooperates with the processing circuitry to receive and store member-specific contributed data submitted by each member, and aggregates the member-specific contributed data with member-specific contributed data contributed by other contributing members, wherein the stored and aggregated member-specific contributed data is de-identified from the stored member-specific account data; and a third party interface that permits third party access to the aggregated member-specific contributed data without permitting third party identification of respective contributing members.

In certain of these embodiments, the second database is maintained by an administrative entity that administers the third party interface, and wherein the administrative entity is precluded from linking aggregated member-specific contributed data accessed by the third party to an associated member-specific account in a manner that would personally identify the respective contributing member without permission of the respective contributing member, and/or the administrative entity permits access to the aggregated member-specific contributed data based upon remuneration from the third party, and/or the access to the aggregated member-specific contributed data is based upon smart code and/or a smart contract, and/or the stages of interaction of the third party with the aggregated member-specific contributed data follows a blockchain or distributed ledger protocol comprising ledger entries for stages of interaction by the third party third party interface, and/or the third party interface is configured to cooperate with the processing circuitry to perform searches of the aggregated member-specific contributed data based upon criteria communicated by the third party, and/or the third party interface permits communication by the third party to contributing members without permitting third party identification of the contributing members, and/or the communication is based upon a unique identifier associated with the aggregated member-specific contributed data of the contributing members, and/or the third party interface is configured to permit contributing members to opt-out of communication by the third party, and/or the third party interface comprises pages transmitted by the server, and/or an account database comprises a centralized database maintained by an administrative entity and the processing circuitry is maintained by the administrative entity, and/or the database comprises a centralized database maintained by an administrative entity and the processing circuitry is maintained by the administrative entity.

In still other embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; processing circuitry that, in operation, interacts with data received via the server; an account database that, in operation, cooperates with the processing circuitry to receive and store member-specific account data based upon interaction of a contributing members; a second database that, in operation, cooperates with the processing circuitry to receive and store member-specific contributed data submitted by each member, and aggregates the member-specific contributed data with member-specific contributed data contributed by other contributing members, wherein the stored and aggregated member-specific contributed data is de-identified from the stored member-specific account data; and a third party interface that permits third party access to the aggregated member-specific contributed data without permitting third party identification of respective contributing members; wherein the processing circuitry is configured to attribute a value to at least some of member-specific accounts based upon remuneration provided by the third party for access to the aggregated member-specific contributed data.

In some of these embodiments, the processing circuitry, in operation, processes member-specific account data to establish member-specific accounts, and attributes the value to at least some of the member-specific accounts based upon remuneration provided by the third party for access to the aggregated member-specific contributed data, and/or the value is based upon respective member-specific contributed data accessed by the third party, and/or the value is based upon whether the respective member-specific contributed data corresponds to criteria provided by the third party, and/or a third party interface that permits third party access to the aggregated member-specific contributed data without permitting third party identification of respective contributing members, and/or the second database is maintained by an administrative entity that administers the third party interface, and wherein the administrative entity attributes a value to at least some of member-specific accounts based upon remuneration provided by the third party for access to the aggregated member-specific contributed data without personally identifying the respective contributing member without permission of the respective contributing member, and/or the value attributed comprises a cryptocurrency, and/or attribution of the value is based upon a unique identifier associated with the aggregated member-specific contributed data of the contributing members, and/or the third party interface is configured to permit contributing members to opt-out of access by the third party to their respective member-specific contributed data, and/or the third party interface comprises pages transmitted by the server, and/or an account database comprises a centralized database maintained by an administrative entity and the processing circuitry is maintained by the administrative entity, and/or the database comprises a centralized database maintained by an administrative entity and the processing circuitry is maintained by the administrative entity.

In still further embodiments, a system comprises a server that, in operation, serves interface pages to contributing members of an aggregation community for receipt of member-specific account data and member-specific contributed data, the member-specific contributed data comprising omic and/or phenotype data submitted by each contributing member or data derived therefrom; processing circuitry that, in operation, interacts with data received via the server; an account database that, in operation, cooperates with the processing circuitry to receive and store member-specific account data based upon interaction of a contributing members; a second database that, in operation, cooperates with the processing circuitry to receive and store member-specific contributed data submitted by each member, and aggregates the member-specific contributed data with member-specific contributed data contributed by other contributing members, wherein the stored and aggregated member-specific contributed data is de-identified from the stored member-specific account data; and a third party interface that permits third party access to the aggregated member-specific contributed data; wherein the processing circuitry is configured to select a portion of the aggregated member-specific contributed data for access by the third party based upon criteria provided by the third party via the third party interface.

In certain of these embodiments, the third party interface is configured to define a secure sandbox memory to which the portion of the aggregated member-specific contributed data is transmitted for access by the third party, and/or the secure sandbox memory comprises a secure cloud service site, and/or the secure sandbox memory and/or logic does not permit downloading of the accessed portion of the aggregated member-specific contributed data by the third party, and/or the third party interface permits third party access to the portion of the aggregated member-specific contributed data without permitting third party identification of respective contributing members, and/or the second database is maintained by an administrative entity that administers the third party interface, and wherein the administrative entity permits access to the aggregated member-specific contributed data based upon remuneration from the third party, and/or the access to the aggregated member-specific contributed data is based upon smart code and/or a smart contract, and/or the third party interface permits communication by the third party to contributing members having member-specific contributed data in the portion of the aggregated member-specific contributed data accessed by the third party, and/or the communication is permitted without permitting third party identification of the contributing members, and/or the third party interface is configured to permit contributing members to opt-out of having their respective member-specific contributed data included in the portion of the aggregated member-specific contributed data accessed by the third party, and/or an account database comprises a centralized database maintained by an administrative entity and the processing circuitry is maintained by the administrative entity, and/or the database comprises a centralized database maintained by an administrative entity and the processing circuitry is maintained by the administrative entity.

DRAWINGS

These and other features, aspects, and advantages of the present invention will become better understood when the following detailed description is read with reference to the accompanying drawings in which like characters represent like parts throughout the drawings, wherein.

Figure 3:
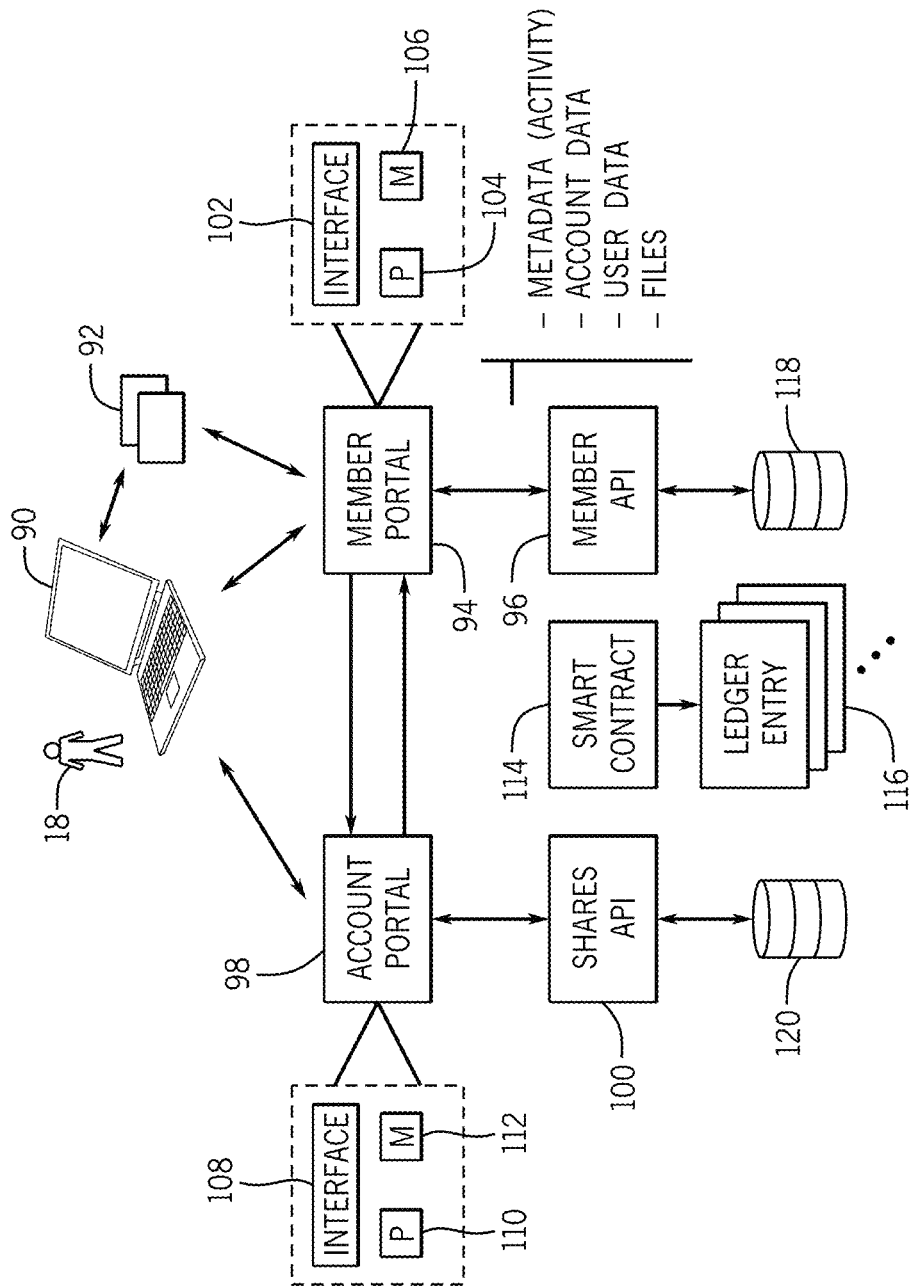
Figure 4:
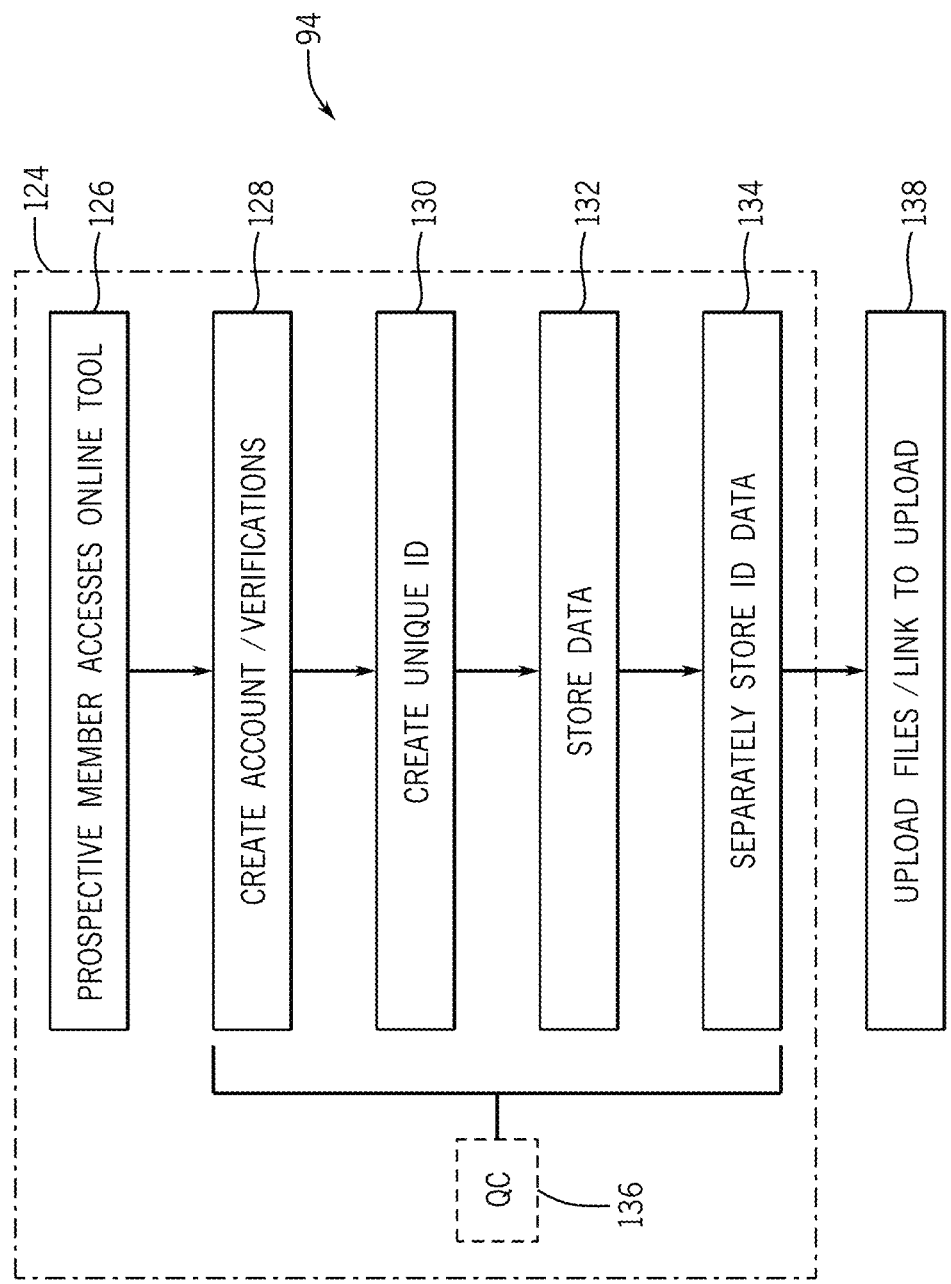
Figure 5:
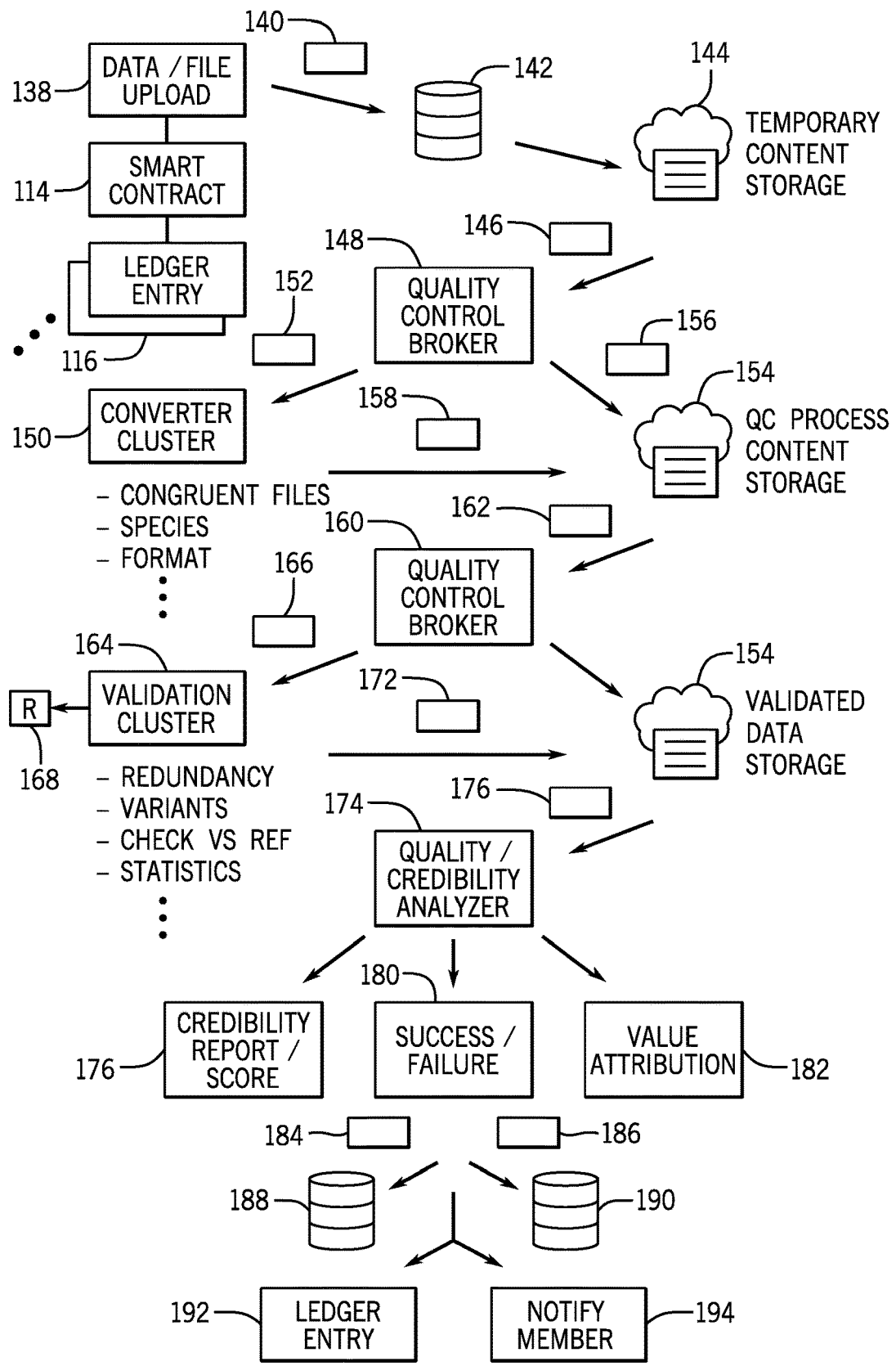
Figure 6:
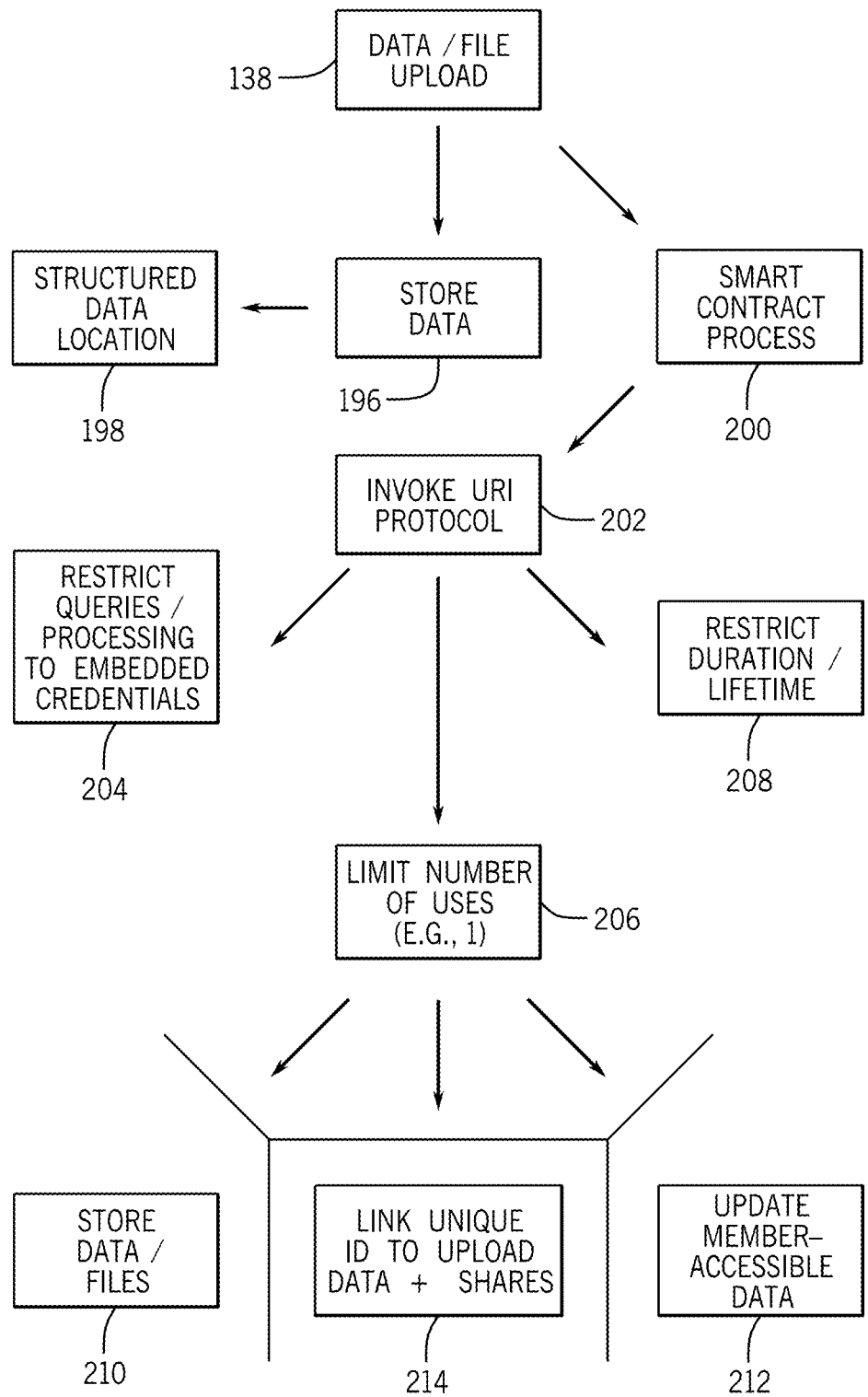
Figure 7:
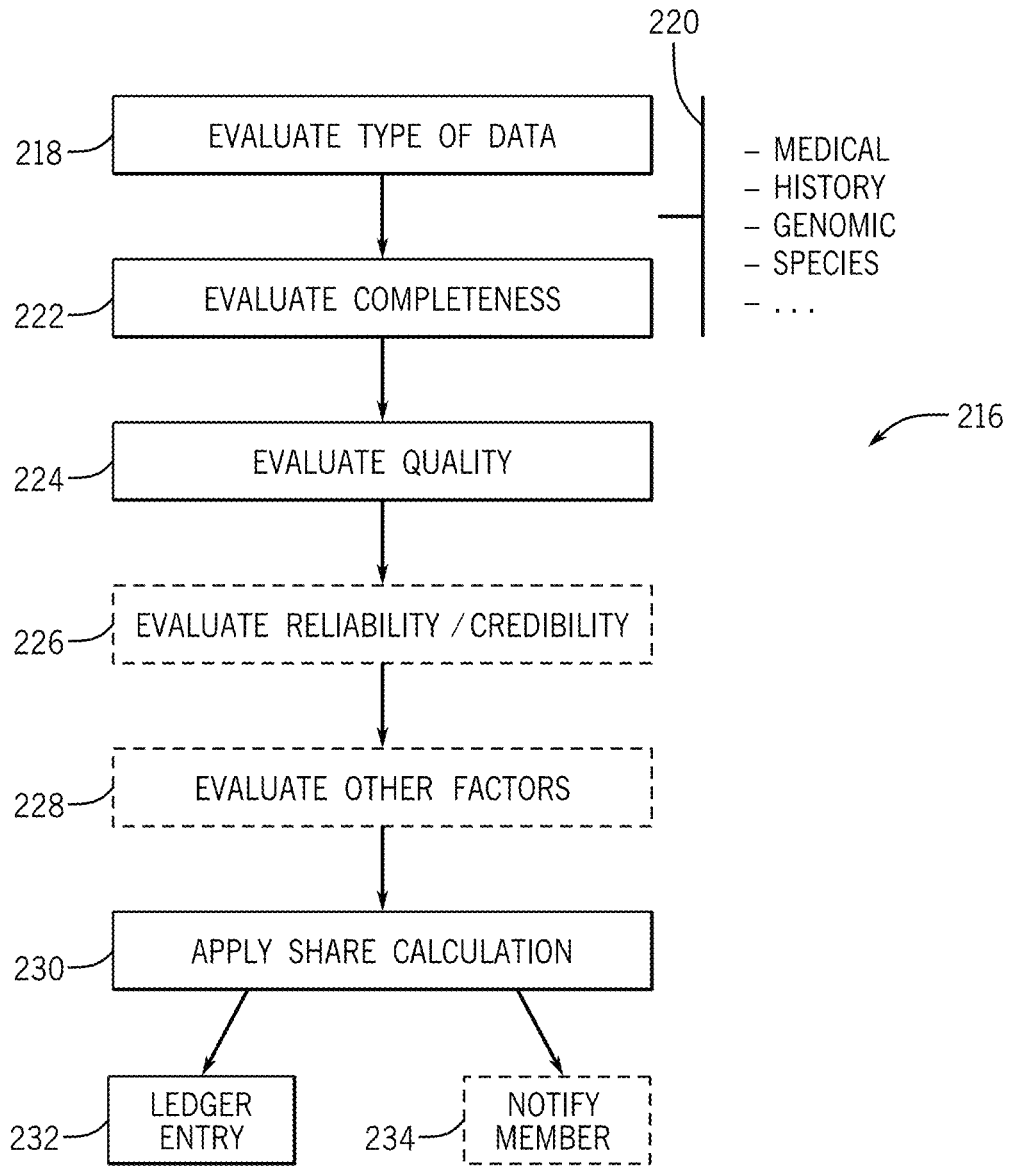
Figure 9A:
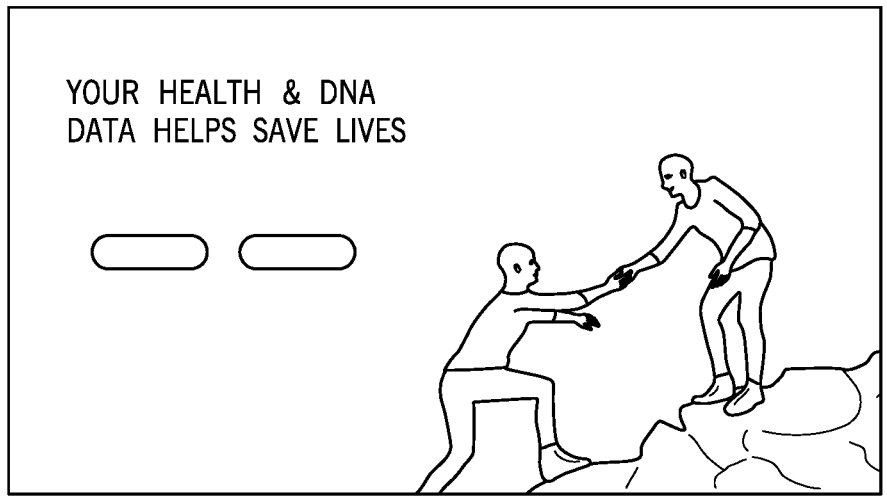
Figure 9B:
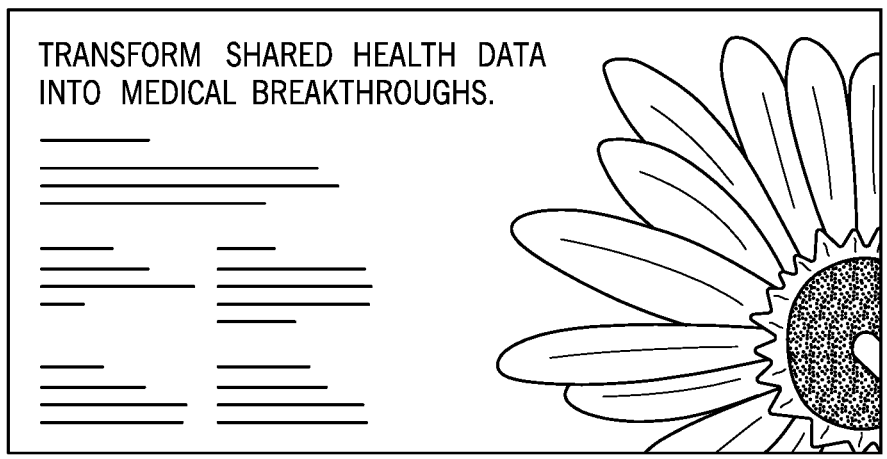
Figure 9C:
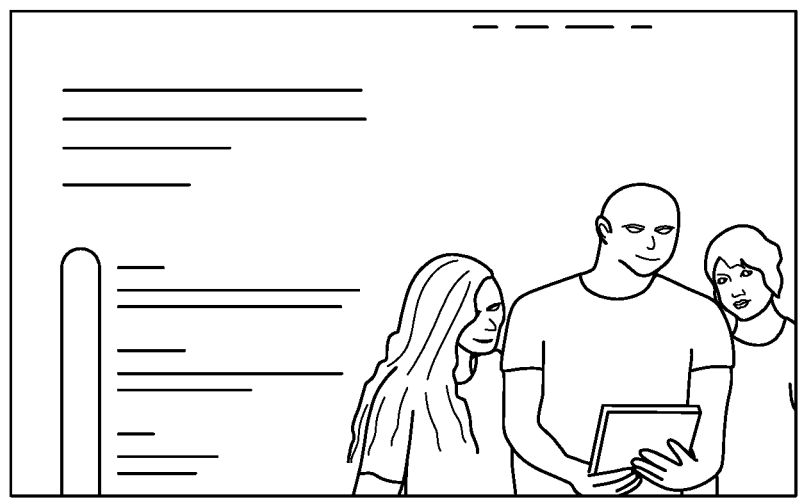
Figure 9D:
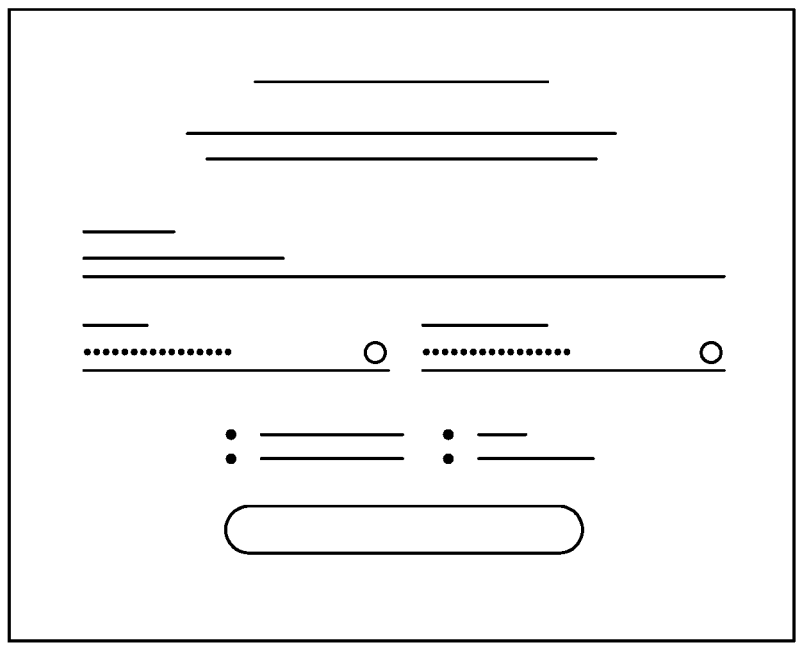
Figure 9E:
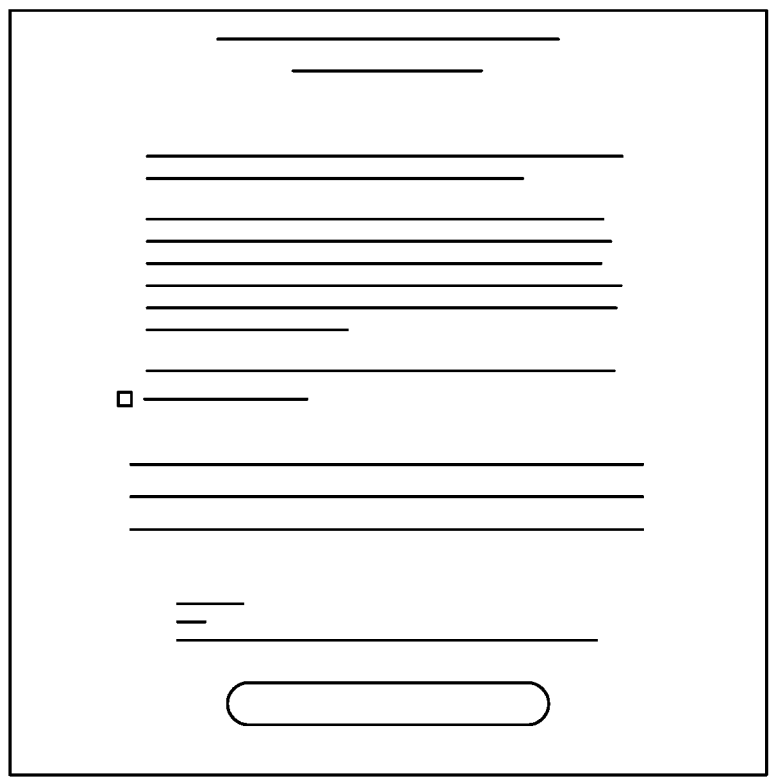
Figure 9F:
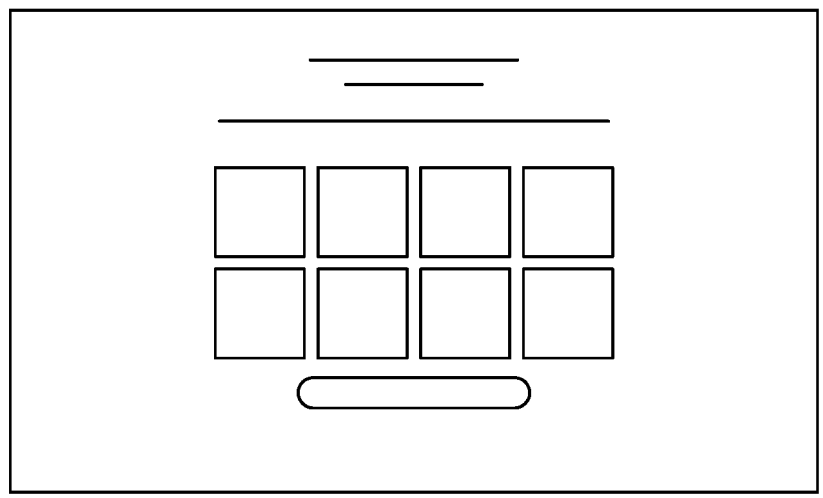
Figure 9G:
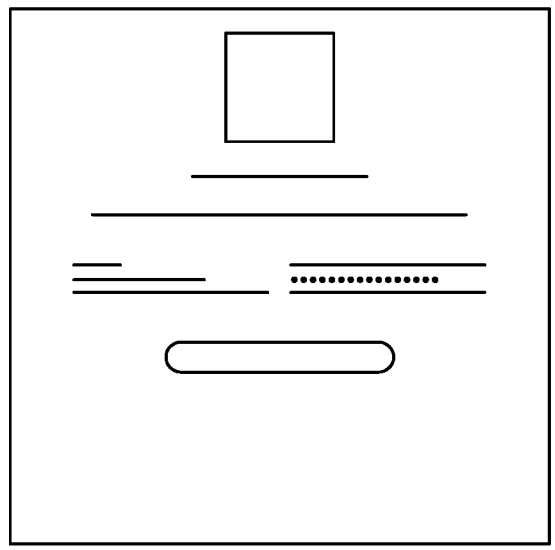
Figure 9H:
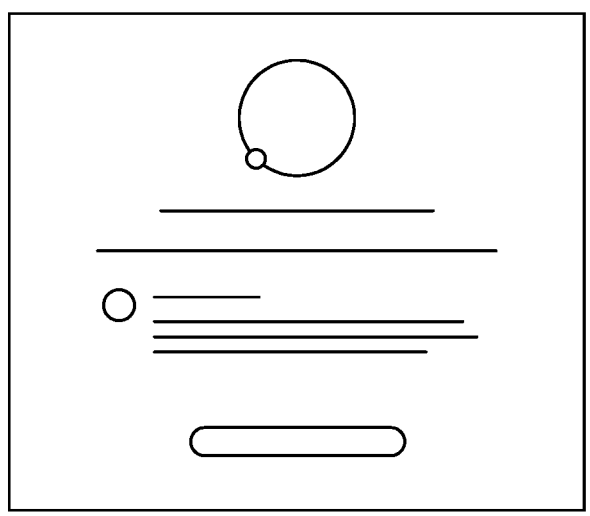
Figure 9I:
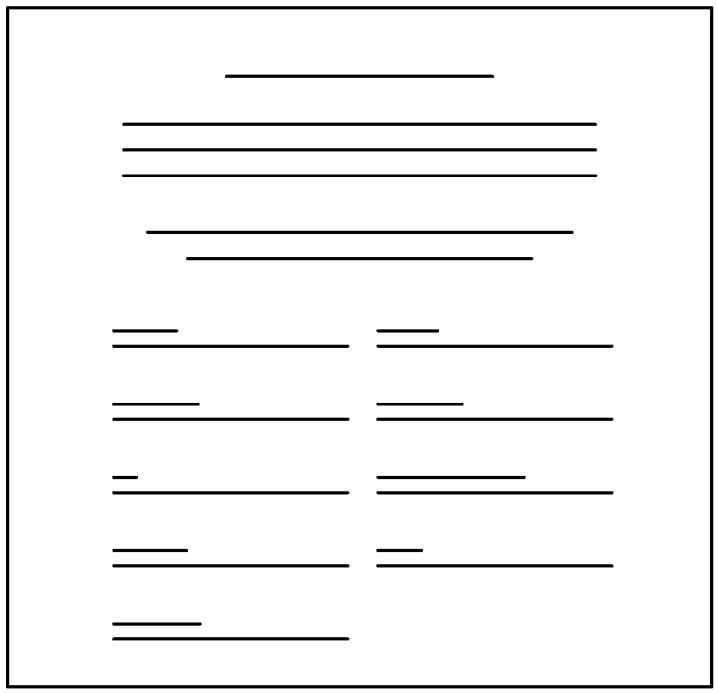
Figure 9J:
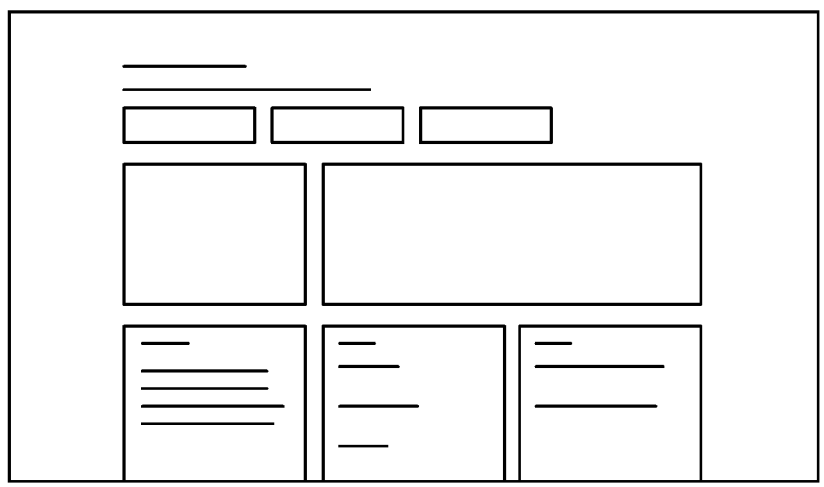

FIG. 3. is a diagrammatical representation of an example account initiation and member interaction process;

FIG. 4 illustrates example operations in the process of FIG. 3;

FIG. 5 is a diagrammatical representation of an example process for member data and file processing and quality control;

FIG. 6 is a diagrammatical representation of an example process for transparent confidentiality in processing of member data and files;

FIG. 7 illustrates example operations in value or share attribution;

FIG. 8 illustrates an example share table of the type that may be used to calculate value or shares for member data; and FIGS. 9A-9J are example interface screens for creating an account and for transferring data and/or files for aggregation in the system.

DETAILED DESCRIPTION

System and Method Overview:

The inventions disclosed here aim to build the world's first and largest human health database that is owned or substantially owned by its community and designed to have key functions powered by trusted, transparent, and tamper-evident data management and data processing technologies, such as blockchain. Through community participation and rewards towards the greater good of human health, the system may create a dynamic, secure, and longitudinal database along with a supporting ecosystem. By making this database available to researchers, the system intends for discoveries to lead to new treatments, increased actionability, and greater predictive power of genomic information for disease and wellness applications. The personal health impact, societal health benefits, and economic value that will be created through clearer associations between genomics and health outcomes can be realized in myriad ways, including accelerating a true era of precision medicine and preventative healthcare.

Despite advances in genomics technology that make the science more accessible than ever from a cost perspective, modern science, research and medicine are still far from broad and lifelong adoption of genomic information and phenotypic information required to understand social determinants of health for many reasons including information complexity, reimbursement of genomics by payers, and lack of common frameworks around data interpretation, usage, and management. One of the most powerful challenges to the genomics trajectory and impact opportunity, especially in the healthcare system, is that genomic information is largely regarded as not informative, actionable, or predictive enough based on limited scientific evidence. To unlock the power of the genome and its potential for discovery, science, research, and medicine, the present techniques aim to providing a new platform for research.

Genomics data is now plentiful, and with continued lowering of acquisition costs it will become more plentiful, while the true issue in unlocking its potentially enormous benefit is personal data aggregation and organization to enable discovery. With that in mind, the present inventions address four primary issues that have hindered genomics and health research:

The scale and scope of discovery datasets have been insufficient for discovery and broad applicability of discoveries to the widest population. Researchers require more samples, more data types (e.g., DNA, microbiome, broad phenotypic information, health history, lifestyle, environment, nutrition), and greater diversity (e.g., gender, ethnicity, age, socioeconomic). Additionally EHR datasets, for example, often lack outcomes from prescribed treatments or even if a patient followed recommended treatments.

The data in databases have lacked a harmonized structure; they cannot be aggregated for calibrated and reproducible discoveries. The ontology and nomenclature used is often not standardized.

Data is "siloed" and will likely remain isolated, despite calls to share data. Most institutional incentives and business models are to retain data (because that is what their business or laboratory was established to do, what their shareholders and stakeholders expect them to do), and, in many instances, consent was not granted from the individual to release their data for research.

People have been treated as specimen sources and partners with tremendous value for medical research. Genomic research has been disease-centric as opposed to being people-centric. People care about their holistic health, which includes both prevention (to maximize wellness) and treatment (during sickness). The current health industry only rewards disease treatments.

When enabled, individuals seek involvement as research partners with the opportunity to fight disease, especially if they are themselves managing a specific condition. In addition to the need to accelerate our understanding and treatments of common complex disease, there are approximately 7,000 different types of rare disease and disorders that afflict 30 million people in the United States that remain a mystery. Similar to the United States, Europe has approximately 30 million people living with rare diseases. An estimated 350 million people worldwide suffer from rare diseases. Healthy people also bring tremendous research value, not only as controls in disease study but also as study subjects to understand how they have avoided disease.

The systems and methods disclosed below may aid to unlock the power of the genome by unlocking the potential for discovery with the largest aggregation of genomic, health, and Real World Evidence data ever assembled. By engaging individuals proactively, responsibly, and with shared equity, a purpose-driven deep engagement may be engendered that will lead to an information-rich, active, and longitudinal data community. Through a silo-free, people-centered effort, a scale and scope may be achieved to enable research for a wide range of diseases, both common and rare, as well as to increase understanding of healthy states. A platform of this magnitude architected with data management techniques such as blockchain smart contract capability and with technical extensibility to ingest data associated with new monitors of health states (e.g., wearables), may have the statistical power to reveal the genomic and other underpinnings of disease and also to detect associations between nutritional, environmental, or other exposures to health outcomes.

Genomics is the study of the function and the evolution of genomes. In humans, this typically refers to the 23 pairs of chromosomes and mitochondrial DNA that make up the full complement of DNA present in every cell. Many hereditary disease can be traced to specific gene mutations observable in the DNA code. To date, genomic research studies have identified genetic causes of hundreds of traits and diseases, including breast cancer, high cholesterol, rheumatoid arthritis, schizophrenia, height, atrial fibrillation, and responses to various medications. These studies not only provide diagnostic value for families and individuals but, moreover, provide meaningful insights into gene function and disease mechanisms that enable better drug design and targeted treatments.

During the last decade or so, genome-wide association studies or GWAS, mentioned above, that utilize common variants in the genome, instead of analyzing the whole genome, have emerged as the primary method of discovering genetic variants associated with complex traits and disease. The GWAS approach was utilized primarily due to economics. The measurement of hundreds of thousands of common variants in our genome was greater than one-thousand times less costly than acquiring 3.3 billion bases in whole genome sequencing studies.

Although GWAS studies have successfully identified thousands of common genomic variants that contribute to diseases, each variant rarely accounts for more than a small fraction of disease causation. The full genome, including rare genomic structural variants detected through direct DNA sequencing, the microbiome, the epigenome, and other environmental factors are together thought to explain the vast majority of disease impacting human health. Detailed genome sequencing of millions of individuals will sometimes be required to fully understand genetic contributions to disease and health.

In summary, the causes of many genetic diseases remain stubbornly hidden despite advances in technology to read whole genomes of individuals cost-effectively. This is in part due to the various complexities of the challenge, such as the polygenic link to disease or interactions with genome and lifestyle, the fact that most diseases are diagnosed based on symptoms and are not always a single disease at the molecular level, and that some genomic causes of disease are not included in the GWAS tests. The scope, scale, and harmonized data architecture of the present disclosure will help reveal genotype-phenotype associations that otherwise could not be found due to lack of statistical power and/or data interoperability.

Precision medicine proposes to invert the healthcare framework by recognizing that each patient is biologically and phenotypically unique. Rather than clinical trials to determine whether a therapy is safe and effective for most of the population before it is available to all of the population, personalized medicine applies real world evidence technology to "big data" to investigate whether therapies will be effective for that specific patient and, equally important, if it will not be effective and potentially harmful for that patient.

This distinction is important because many diseases are unique to the individual. Diseases manifest and progress differently in different people (or more generally, different organisms), and treatments that are effective for one person may fail altogether for another. The promise of precision medicine is that patients will respond to targeted therapies and avoid the all too common, ineffective, costly, and often damaging treatment regimen.

Our DNA represents a "blueprint" that is individually unique and can be leveraged in precision medicine and health. Futurists project that everyone will have genome information as a resource, on file and actionable, before they become ill so that it can be leveraged to maximize the health strengths that individuals naturally possess, while avoiding an individual's inherent health weakness through lifestyle decisions. Precision medicine will increasingly leverage advances in big data to analyze large amounts of genomic data and apply the understanding gained to individual diseases and treatment. As stated, for centuries, the engine of medicine has been the clinical trial that poses the central question, "what is effective for most people?". Genomic data, in conjunction with real world data and the technology developed to compute, analyze, and understand these data is increasingly regarded as the engine of medicine going forward. Research enabled by the disclosed techniques may drive the development and application of more genome-guided therapeutics, ensuring that the right medicine is given in the right dose to the right patient at the right time.

Moreover, the popularity of the direct-to-consumer (DTC) genetic testing market segment signals an ever-expanding paradigm shift among consumers who are seeking more individualized health insights and greater control over their own healthcare. With advances in genetic testing technology at accessible cost points and the mainstream nature of personalized medicine, DTC laboratory testing is becoming increasingly popular. Since the 1980s, consumers have pushed for access to their laboratory results, but access became slow to evolve due to concerns by doctors and regulators that consumers may try to self-diagnose without understanding the complexity of the data. Likewise and following suit, consumers are becoming health hobbyists and self-quantifiers, taking individualized healthcare into their own hands. Consumers have become medical consumers as well as patients. This has created a shift in the doctor/patient relationship as individuals have become more knowledgeable about their own health, view themselves as unique biologically in a one-size fits all healthcare system, and want more control over their personal information and treatment decisions.

Almost 20 years since the Human Genome Project, consumer-directed genomic testing has become practically routine with over 20 million individuals purchasing genomic products ranging from specific gene tests, to genotyping arrays with entertaining applications in genealogy and wellness, to sequence profiling of germline DNA or tumors to provide targeted treatment guidance. As technological advances continue to drive down the costs of genome sequencing, from approximately $1,000 per genome today to $100 or less within the next few years, there will be an increasing availability of this highly valuable health data. Several trends are continuing to shape the DTC market including the growing demand for maximizing wellness, early disease detection and diagnosis, personalized medicine, importance of disease monitoring, and expanded digital monitoring and sensing technologies. In addition, consumer-directed but physician mediated genomic tests are emerging.

There are a variety of reasons people participate in biomedical studies. Some reasons may be personal, such as the desire to know one's ancestry and disease predispositions. Other motivations may be broader or more altruistic, such as the desire to improve human health and society. In all cases, there must exist a level of trust between the research participant and the investigators that they are pursuing a shared goal. Unfortunately, failure of researchers to maintain the trust of study participants can have lasting negative effects on science as a whole.

Privacy, security, and trust are core pillars of the present disclosure and are reflected in the systems, methods, and technology disclosed here to ensure the best possible management and maintenance of information. It is important to note that the techniques are based on based on de-identified metadata, the control and ownership of which remains with the contributing member.

Nearly all medical research requires some form of informed consent by, or on behalf of, the research participant. In this process, the individual enrolling in the study provides their voluntary agreement to participate in the research, and understands the risks associated with their participation. Sometimes the field of the informed consent is very narrow, such as in clinical trials for pharmaceutical companies interested in deep, focused studies of a particular biological function or disease. In other cases, the consent can be broad, enabling future exploratory studies into research questions that are yet to be defined. Occasionally, data collected as part of a research study can be shared and/or re-examined by other investigators for a secondary study. In practical terms, this variability means the usefulness of a collection of data sets is circumscribed by the subset with the narrowest terms of consent. This presents a clear scalability problem and limits the utility of historical datasets, if the individuals comprising the data are unavailable to provide a more broad informed consent.

One of the primary use cases for mining genomic databases is the opportunity to identify new drug targets. Rational drug design leverages biological and molecular understanding to develop therapies targeted at disease pathways and mechanisms of action, and can be applied to both common and rare diseases. By understanding the genetics of disease and the role mutated genes play in the cell, drug developers can pursue a more "rational" design approach. A recent example of how rare genetic mutations can lead to understanding of the biology underlying common diseases and lead to cures for the broader population came from the study of a small sample of patients with familial hypercholesterolemia (FH). FH is suspected when LDL-cholesterol is above 190 mg/dL in adults and above 160 mg/dL in children without cholesterol-lowering treatment and poses a life-long risk of severe cardiovascular disease. Based on these family studies, researcher discovered a monogenic form of FH that is due to severe mutations in one of three genes: LDLR, APOB, or PCSK9. This observation led to the development of monoclonal antibodies to lower LDL by blocking the PCSK9 gene, and has now been commercialized by five different drug companies offering the therapy to lower cholesterol in the general population, not just those with FH.

Currently, an estimated 90 percent of potential medicines entering clinical trials fail to demonstrate the necessary efficacy and safety, and never reach patients. Many of these failures are due to an incomplete understanding of the link between the biological target of a drug and human disease. By contrast, medicines developed with human genetic evidence have had substantially higher success rates and patient care has benefited.

Moreover, as noted above, much of the genomic data and phenotype data collected by commercial genomics companies, laboratories, and pharmaceutical companies remains siloed and inaccessible to the research community. In some cases, the reason is inefficient database design or poor data management practices. The pharmaceutical industry lags behind other sectors in several indicators of digital maturity. More often, however, is the strategic decision to attempt to extract value from data themselves, hampering meaningful data sharing across organizational boundaries. Additionally and importantly, the revenues of their data monetization strategies have never been shared with those who contributed the data. Often discovery companies go to great lengths and expense to ensure data provenance, completeness, and integrity, and hence these institutions attribute a much lower value to data from other entities.

Many pharmaceutical companies have begun integrating patient data from applications, wearable devices, and electronic medical records (EMRs) to improve healthcare and make discoveries about disease. Technology companies are also entering this market. Given these trends, it seems unlikely that the pace of future research will be limited by information technology problems, but rather hindered by corporate self-interest. Another major challenge is the current state of EMR implementation. While adoption of EMRs is almost at 100 percent in the United States, in this new health economy, effective implementation of EMRs is still in the early stages. The standards deployed in terms of how they are used and the medical terminology adopted varies greatly institution to institution. Standards for medical nomenclature and inter-relationship, or ontology, can vary greatly and, in some cases, health care providers still rely on the comments section of the patient record to record important information. Historic clinical records are often simply PDF files or pictures of hand written medical histories. Ingesting, curating, and harmonizing this information to the quality required for identifying links between our genome and our lifestyle to disease remains a major task and challenge.

All of these factors contribute to creating what may be termed "friction" in the collection, aggregation, storage, analysis, and use of tremendous quantities of valuable data. By aligning with data contributors as research partners and placing their data within their control, the present inventions aim to reduce or eliminate such friction and to liberate data from these silos through an active and engaged contributor community.

The intersecting trends of inexpensive and accessible personal DNA testing, broad implementation of EHR systems, and nearly frictionless transaction capacity create significant opportunity. First, individual DNA testing is going mainstream, led by consumer-friendly companies like 23andMe, Ancestry.com, MyHeritage, and National Geographic in partnership with Helix. Second, EHR systems are mandated in the U.S., as is the requirement for institutions to provide individuals their EHR records upon request.

Third, with the advent of big data technologies and machine learning, its possible to find statistically relevant signals out of the noise of the data.

In addition to DTC products, there are new and emerging opportunities for individuals to receive their DNA information that can be brought to the present system by members. Consumer-directed and physician-mediated wellness offerings are growing in popularity as individuals look to work with a healthcare provider to maximize their wellness. Large-scale population health projects like the United States National Institute of Health's All of Us Research Program will accelerate individual's access to their genomic information. Certain disease foundations also have very engaged patient communities and funding for genomics research, but typically lack the interest and skills to stand up and manage a genomics database.

Furthermore, as discussed further below, the maturing blockchain technology provides an extremely low-friction opportunity to enable data sharing and database monetization through smart contracts. Blockchain smart contracts also enable decentralized control of data and immutable ledger to record transactions.

Together, these forces create the ideal time and place to develop a shared, secure, and owner-controlled medical research data platform.

To date, obtaining large volumes of high-quality biological, health, and lifestyle data has been a major challenge in the medical research field. By being independent and agnostic to which DNA analysis technology platform or brand that was used, the present system can gather data from multiple contributor sources without conflict of interest. One's genomic information can be acquired by companies that help to learn about ourselves, while also being shared with the member community (and interested third parties) in support of disease and therapy discovery.

The database will earn money through the sale of access to its de-identified pooled data, metadata, and research findings by the system and its members to third party partners in the research and medical industry and by supporting clinical trial activities such as recruitment, data monitoring, and post trial recontact. System administrators may share in the proceeds or earn a fee for enabling transactions between buyers and sellers of data.

Information inputs into the database may typically include self-reported information, medical data, microbiome data, wearable data, and DTC testing product data files. The platform is extensible such that future data inputs such as methylation data and proteomic data can be collected. The collective de-identified data creates a pooled data metadata resource for nonprofit and for-profit research to be conducted with the help of enabling informatics and artificial intelligence resources. As value is derived from the access to and discoveries from the database, that value flows back to the community and is deposited in their unique wallet or account. Community ownership in the database means that when commercial organizations pay market prices to access the database, the profits from these transactions will flow back into the accounts of the community members, such as based on a member's percent ownership.

As the database grows, it will become increasingly valuable to the entire medical research industry. Therefore, as an owner, the data contributor's stake in the database and/or dividends increases as they deposit more genomic, phenotypic, and biometric (e.g., wearables) data. Unlike other prior art approaches, proceeds generated by selling access to the data, for example to pharmaceutical companies, will be apportioned among the community, and thereby directly benefiting the data contributors. Contributors will always retain the ability to retract their consent by returning or forfeiting "value" (e.g., coins, tokens, shares) provided as compensation for contributing data. Contributors may be able to retain dividends received as a result of their ownership while their data was included in the database.

Community ownership addresses many of the challenges that exist due to a) prevalence of data silos, b) lack of trust in commercial entities monetizing the individual's data, c) lack of trust in research activities that go dark once information is provided, and d) lack of a single data standard hindering large-scale biomedical research studies.

A member may receive ownership of the database in the form of shares. The number of shares will increase without upper bound as more data is added to the database and will only decrease in the event that a member decides to rescind consent, in which case the member's shares may be forfeited. Each member's ownership percentage is calculated by dividing the member's shares by the sum total of the shares of all members in the community.

Re-contacting subjects from previous research projects to evaluate outcomes over the longer term may be possible. Contacts with members, also available only if agreed upon by the contributing member, may make use of value-added apps available to community members, and cohort sequencing (genome or exome) or genotyping by research organizations and pharmaceutical companies through preferred data generators. Moreover, other operations and contacts may provide access to population health insights, partnering rights to the community ecosystem, comprehensive offering of value-added services for community members (e.g., services for genomic data insights based on their individual profile), monetization of community-owned equity stakes in drug, biotech and medical discovery companies that have used the database as means to create intellectual property, and service access to adjacent markets.

By way of example, below is one example of how an individual may be rewarded as they join the member community and contribute information:

An individual joins the community, provides broad consent for use of the data in studies, and contributes a full genome sequence. The system establishes a unique account and recognizes the contribution with shares that reflect ownership in the database. The individual's ownership can be calculated at any point in time as the individual's shares divided by the sum of all members' shares.

Once an individual becomes a community member, the system may reaches out to the member with a request to provide personal information in the form of EHRs, health and environmental surveys, and/or biometric data. As members provide this additional information, they receive additional shares in the database.

The first focus of the platform will be driving associations between genomic information and health outcomes. However, as science advances and other "omic" technologies such as microbiome sequencing, pathogenomics, metabolomics, or proteomics become less expensive and more accessible to patients and consumers, the platform may be scalable and capable of incorporating these other data types to further researchers' ability to understand and digitize the medical essence of a human being.

As noted above, many different types of data, and approaches to membership and value attribution may be envisages for the present techniques. But of particular interest is genomic and related data. In the present context, reference may be made to "omic" information, which may include, without limitation, genomic data, microbiomic data, epigenomic data (e.g., methylation data), pathogenomic data, transcriptomic data, enviromic data, and proteomic data. Genomic data includes, without limitation, genotype data (e.g., single nucleotide polymorphism data, short tandem repeat data, microsatellite data), haplotype data, and whole or partial sequence data of genes, chromosomes, exomes, and genomes (e.g., fully assembled genomes, partially assembled genomes). Genomic data may cover both the germline genome and the somatic genome. In the present techniques, collecting and aggregating omic information pertaining to multiple subjects into a centralized database allows the information to be used for population or disease studies. For example, central database aggregation is useful to identify statistically significant relationships between certain genetic elements and a particular disease or phenotype information. Such relationships, when identified, are useful for identifying therapeutic targets and designing therapeutic approaches for treating or diagnosing disease. When a particular genetic locus or allele is identified as being significantly associated with a particular disease, for example, a therapeutic regimen that targets that locus or allele can be deployed (e.g., genetic modification, testing of a drug known to target the locus or allele).

While omic and phenotype data has been obtained for a number of subjects, it has become apparent there are significant obstacles to collecting, aggregating, and managing it in a centralized database. Systems provided herein have been designed to overcome these obstacles for collecting and managing omic data, phenotype data, and/or other types of related data in a centralized database, and generally are designed for contributors of data having an ownership interest in the data deposited. Systems described herein in certain aspects are designed to (i) provide value, and (ii) provide an ownership interest in the associated database, for omic data, phenotype data and other health-related data deposited into the database.

In certain aspects, a system provided herein (i) includes a central database that includes omic data and/or phenotype data, and (ii) generates a system account specific for the subject to whom deposited data pertains. The term "system account" is utilized synonymously with the term "wallet" herein. A system sometimes includes a user interface that facilitates a depositor to deposit data pertaining to a subject from a user account into a database of the system.

Ownership in the database generally is directly associated with an opened system account. After the depositor deposits data into the database, the system often will calculate a fraction of ownership in a database for the system account. In some embodiments, the system will, after a depositor deposits data into a database for the system account, (i) transfer an amount of currency into the system account based on the data unit deposited, and (ii) calculate a fraction of ownership in the database for the system account. The fraction of ownership is then associated with the system account. A depositor can enter different data units into the database on multiple occasions and the system often will re-calculate fraction of ownership for the system account after each of the occasions (e.g., the system often will (i) transfer an amount of currency into the system account based on the data unit deposited, and (ii) re-calculate a fraction of ownership in the database for the system account).

Fraction of ownership for a system account can be calculated in any suitable manner. Fraction of ownership for a system account sometimes is calculated according to the sum of data units of each type of data unit deposited into the database associated with the system account divided by the sum of all data units of each type of data unit in the database. In certain embodiments, fraction of ownership for an account is calculated according to Formula A:

$$F=x/y \qquad \text{Formula A}$$

where F is the fraction of ownership; x is the sum of $((W1)(\text{sum of data units of a first type of data unit})+(W2)(\text{sum of data units of a second type of data unit}) \ldots +(Wn)(\text{sum of data units of an n type of data unit}))$ associated with the account; y is the sum of $((W1)(\text{sum of data units of the first type of data unit})+(W2)(\text{sum of data units of the second type of data unit}) \ldots +(Wn)(\text{sum of data units of the n type of data unit}))$ associated with all accounts; and $W1, W2 \ldots Wn$ are optional weighting factors. In such embodiments, "n" in "Wn" and "n type of data units" is an integer of 3 or greater (e.g., 3-100, 3-50, 3-25, 3-20, 3-15, 3-10, 3-9, 3-8, 3-7, 3-6 or 3-5), and " . . . " is a sequential series, where, for example, if n is 5, the series includes a first type of data unit, a second type of data unit, a third type of data unit, a fourth type of data unit, and a fifth type of data unit, and optionally includes W1, W2, W3, W4 and W5.

In certain embodiments, fraction of ownership for a system account is calculated according to Formula B:

$$F=\text{sum}(Cixi)/y \qquad \text{Formula B}$$

where F, x and y are as defined as above; C is a pre-defined value or weighting factor between 0 and 1 or greater than 1; and $\text{sum}(xiCi)$ is the sum of all individual data entries multiplied individually by weighting factor C, and then summing the individual products for a determination of F.

If value (e.g., an asset amount) is received as consideration for accessing or extracting information derived from data in the database, or received as consideration for use of data in the database, the system often will transfer a fraction of an asset amount to each system account according to the fraction of ownership calculated for the system account. Any suitable type of currency may also be transferred to a system account. A system account sometimes includes one or more types of asset types, non-limiting examples of which include cash in a particular currency (e.g., tangible currency, cryptocurrency), equity (e.g., one or more shares of a stock, or ownership units, or Ethereum ERC-20 tokens), a fixed income asset (e.g., one or more bonds) and a commodity. In certain embodiments, one type currency its utilized in a system and all system accounts receive the currency. Currency transferred to a system account sometimes is a cryptocurrency. A cryptocurrency utilized sometimes is generated on a platform and/or operating system having one or more of the following features: open-source, public, blockchain-based, distributed computing, distributed ledger, and having smart contract or scripting functionality.

A system can include one or more databases into which omic data, phenotype data and other health data is deposited. A subject can be any type of organism (e.g., human, feline, canine, ungulate). A particular database in a system often includes data pertaining to a particular type of organism (i.e., one database that contains only data pertaining to human subjects; another separate database for data pertaining to feline or canine subjects; another database for data pertaining to human pathogens). A depositor often is the subject to whom the data pertains (i.e., for human subjects) A depositor sometimes is a person having a relationship to the subject to whom the data pertains. A relationship can be, without limitation, a legal relationship (e.g., human agent, custodian and/or guardian of a human subject), a familial relationship (e.g., a parent or other family member of a human subject), and a companionship (e.g., a human owner of a feline or canine subject). A depositor also may deposit omic data from the depositor's surrounding environment, non-limiting examples including omic data from soil microorganisms and/or microorganisms from the built environment around the depositor.

A system sometimes includes one or more security features designed to prevent inappropriate access to an account identification feature. A central database in the system generally stores de-identified data, dis-aggregated data, and features associated with an account sometimes consist of, and are limited only to, (i) ownership interest information, and (ii) currency (if and when currency is transferred to the account). Disaggregation of the data and or the data keys increases security of the data by eliminating single points of failure or vulnerability. A subject's identity typically is not directly present in the central database that contains the deposited data. A subject's identity sometimes is located in a secondary database inside or outside the system. One or more account identification features, such as an account number and/or passcode for example, often are created by an individual and often are transmitted to the system in an encrypted manner. A password often is encrypted on an individual's computer and only known to that individual to ensure the information is transmitted and stored securely. Such account identification information often is not linked to the name of an individual or other direct identifying information for the individual (e.g., not linked to an email address, telephone number or physical address of the individual) in the system.

In the event that an individual, or heir or agent of an individual, cannot locate an account identification feature, a system in some embodiments is configured to transmit an account identification feature to a requestor based on first inquiring and then matching de-identified data in the database. In certain embodiments, a system is configured to: receive a request by a requestor of an identification feature of an account; notify the requestor of required input information features; receive the required input information features; identify (i) an account for which associated data matches the required input information features, thereby identifying a matched account, or (ii) identify no account for which the one or more required data features matches the input information; and transmit an identification feature for the matched account to the requestor if a matched account is identified according to (i).

In some embodiments, the required input information features are chosen from omic data linked to the account, phenotype data linked to the account, non-omic and non-phenotype data linked to the account (e.g., health data, personal data, familial data and environmental data), and sample information from a biological sample from the subject to whom the data in the account pertains. In some embodiments, a biological sample is provided (e.g., saliva or other suitable sample from which a sufficient amount of biological material can be isolated for analysis) and analyzed (e.g., sequencing analysis, methylation analysis and the like). In certain embodiments, a system includes contact information for an individual associated with an account (e.g., in a database separate from omic data, phenotype data and other data). In such embodiments, the system sometimes is configured to provide a notification via the contact information of the request for the identification feature(s) of the account, and transmit the identification feature(s) for the matched account a designated amount of time after the notification if no objection is received (e.g., transmit the identification feature(s) about one week after the notification is transmitted if no objection is received).

In some embodiments, a system matches an account to the required input information features according to one or more data keys. In certain embodiments, each account in a system is associated with one or more data keys, or two or more data keys. In some embodiments each data key is specific for a type of data associated with an account. By way of a non-limiting example, a first data key may be specific for omic data, a second data key may be specific for phenotype data, and a third data key may be specific for non-omic and non-phenotype data (e.g., health data, personal data, familial data and environmental data). In certain embodiments, the data key(s) associated with an account are de-centralized in a system. The data key(s) sometimes are de-centralized via one-way pointers and sometimes are de-centralized by a block chain. Another non-limiting example is storing an individual's data key in an encrypted manner in an account on the block chain with a one way pointer from the personal information to the data key. When the individual successfully provides the required personal information, the one way pointer would provide the encrypted data key. The data key can be encrypted using other personal information, such that identifying the encrypted key only is insufficient to access the actual key. The other personal information can be genetically based, such as predefined genotypes or previously specified non-genomic information.

In some embodiments, a system is configured to analyze deposited data associated with an account and determine whether the data (i) is fabricated or (ii) is not pertaining to or from the same subject to whom other data associated with the account pertains. In some embodiments, a system is configured to determine whether the same data has been deposited for two or more accounts (e.g., the same omic information has been deposited in two or more accounts). In certain embodiments, a system is configured to perform a statistical analysis on data within an account or between accounts (e.g., statistical analysis on omic data) to identify sub-data that is statistically inconsistent with other sub-data. Such statistical analysis can assess the likelihood the data is (i) is fabricated or (ii) does not pertain to the subject or the prescribed species (e.g., a prescribed species of omic data submitted for a pet dog or cat). In certain embodiments, a system is configured to analyze genome variants that include without limitation single nucleotide polymorphisms, indels, short tandem repeats, microsatellites, haplotypes, polynucleotide deletions, polynucleotide insertions, and polynucleotide structural rearrangements. A non-limiting example of such a statistical analysis is comparing a deposited genotyping file to a human reference map to assess the number of rare genotyping variants and their associated frequency in the population. Another non-limiting example of such a statistical analysis is comparing a deposited genotyping file with known haplotype maps to identify linkage disequilibrium. Linkage disequilibrium is the non-random association of alleles at different loci in a given population. In both examples the statistical probability that the deposited file emanated from an individual from the human species can be calculated.

A system sometimes includes a sequential input framework for community contribution to the system, which can facilitate system improvements. Non-limiting examples of elements that can be contributed to a system include educational videos (e.g., for database contributors, prospective database contributors, and/or users of data in the system) and algorithms for analyzing data in the database. Each element for contribution sometimes is segmented into multiple sub-modules, and each module can be sequentially presented to a contributor. In certain embodiments, (i) an element may be segmented into n sub-modules, where n is an integer of 2 or greater (e.g., an integer of 2 to 100); (ii) a contributor is presented with the first of n sub-modules; (iii) after the contributor completes the first of n sub-modules, the contributor is presented with each subsequent sub-module in sequential order after the preceding sub-module is completed, until the contributor is presented with the final nth sub-module; and (iv) after the contributor completes the nth sub-module, the contributed element is consented to and is incorporated into the system. As a non-limiting example, (i) an element may be segmented into three sub-modules; (ii) a contributor is presented with the first sub-module; (iii) after the contributor completes the first sub-module, the contributor is presented with the second sub-module; (iv) after the contributor completes the second sub-module, the contributor is presented with the third sub-module; and (iv) after the contributor completes the third sub-module, the contributed element is consented to and is incorporated into the system. Such a sequential presentation of sub-modules to a contributor may be implemented by a smart contract framework in a system, and completed sub-modules and/or a completed element may be incorporated into a block chain. A contributor may be rewarded after each sub-module is completed (e.g., with currency specific to the system; cryptocurrency).

The privacy and security of information submitted by members is considered of upmost importance. The contemplated system uses all reasonable technical, physical, and administrative controls to protect member personal, genetic, and health information from unauthorized access or disclosure and to ensure the appropriate use of this information. Such information may be defined as follows assuming for this example only the three types of information listed below:

- Personally identifiable information: information that can identify the member, either alone or in combination with other information. This includes protected health information that is identified under the regulations in place in the United States, and primarily HIPAA (Health Insurance Portability and Accountability Act of 1996). This includes account information (name, email address, password, etc.).
- genomic information: information that a member shares with the system based on previous genetic or genomic testing that they have done. These may include results of genomic and similar studies and sequencing, including consumer tests, such as those offered commercially by 23andMe, Ancestry.com, Helix, HLI, or others, or physician-ordered tests.
- health information: information that a member shares based on their medical history. This may include electronic health records (EHRs) from healthcare providers, hospitals, diagnostic labs, etc., health surveys, and other information collected from integrated apps and devices that the member authorizes to share with the system.

To become a member of the system described here, individuals must consent using an online electronic consent, or "eConsent" process, to allow their de-identified genomic and health information to be searched or queried for ethical research brokered by the system or system administrator(s). All genomic and health information is anonymized (or de-identified). De-identified or anonymized information does not identify the member based on individual pieces of information or combinations of information. The member's personal information is removed, such that they cannot be reasonably re-identified as an individual. Their individual genomic and health information is combined and compiled (or aggregated) with other individuals' genomic and health information for the purpose of pooled or population level analysis.

Each type of information is uniquely tagged with a sequence of characters that is determined by a one-way hash function, designed in such a way that it is extremely difficult to reverse engineer the given value. This disaggregated information is stored across separate persistence mechanisms (i.e., private cloud storage sites) as described herein, which increases the barriers for anyone trying to access any member's complete data profile.

The system further maintains a high level of data protection via safeguards such as data backup, audit controls, access controls, and data encryption. Network sites and APIs use Secure Socket Layer (SSL) technology to encrypt all connections to and from the site and APIs to enhance security of electronic data transmissions. Additionally, the system uses the latest standards and processes for securing and encrypting all member information at rest.

In presently contemplated implementations, access to member information may occur in two-ways: (1) by the member directly (see "Account Access by Member" below), and (2) by the system administrator to enable studies contracted between the membership and third party research groups (see "Information Access for Studies").

Account access by member: The member initiating and maintaining an account, and submitting data via interaction with the system is in control of the selection and safety of their password, but the administrator maintains measures in place to assist. In a presently contemplated embodiment, the administrator requires two-step verification for members signing into their account.

Information access for studies: Only de-identified genomic and health information is accessed based on third-party submitted study design criteria. These criteria are used to query the system's database(s) for appropriate information to include in a possible study. The genomic and health information is only identified based on a unique identifier independent from member personal information. Once subsets of information are identified, the information is aggregated and populated in a secure, private "sandbox" within the system's secure cloud service site for analysis by third parties who may be interested in analysis, tests, studies, and research based on the aggregated member data. In some situations (i.e., clinical trial recruitment), the third party may be interested in contacting members directly. The system may enable this via an anonymous process that leverages the unique identifier associated with the members' genomic and health information, which allows the third-party to invite members into a direct communication (but in present embodiments the third party still has no knowledge of the members' personal information). It is then the members' choice whether they will engage in direct contact with the third party or not. Preferences to receive these invitations can be turned on or off within a profile page of each member's account. All information in the system only includes what members voluntarily authorize to share. At any time, members can choose to delete some or all of their shared information from the system, and withdrawal of information will impact the member's ownership or value stake in the system. In all events, the member is the owner of their data.

Moreover, as discussed below, in some embodiments, the system will require that members complete a short form describing the data (e.g., genomic data) they are sharing to better enable subsequent quality assurance checks prior to the transfer of shares to the member. The form will include information such as: name of test provider (i.e., 23andMe, LabCorp, etc.) and type of test (i.e., BRCA, genealogy, etc.). It is contemplated that quality assurance checks will be performed, for example, to prevent randomly generated files and/or to confirm that a file contains human genomic data. Moreover, a check may be performed to ensure that sites for sharing data will employ various spam blocking techniques to suppress bot activities and spammers. Further, uploaded data may be cross-checked against a reference of human genomic data. Still further, a check may be made to prevent duplication of files and/or to assess a level of overlap (if any) of content with existing files or data. If any exists, the uploaded data is compared against overlapping content in previously shared files for consistency. Content that has greater than 95% overlap, for example, may be considered a duplicate file and not accepted. It should be borne in mind, however, that many different types of data may be of interest and may be entered, accepted, and stored in the system (with a corresponding value or share attributed to it), and as new data types are accepted the quality assurance processes will evolve to continue to ensure accurate and appropriate data is accepted into the database(s) and credited to members for share acquisition.

Terms and Concepts

Through the present disclosure, certain terms and concepts are referred to in embodiments of the technology described. These may be understood by their ordinary and customary meaning in the art, and in view of any special meaning used in the present context, as will be understood by those skilled in the art. Some of the terms and concepts include:

Data member-specific account data: information relating to a members residence, contact info, tax filing number, ownership stake, birth date, etc.;

member-specific contributed data: personal, health, medical, environment, historic, and omic data that is specific to a person contributing the information;

"data": depending upon the context, the general term "data" may apply to account data, contributed data, data based upon one or both of these, or to processed and/or aggregated data;

data derived from contributed data: metadata, summarized data, or data emanating from a logical or mathmatical analysis of the member data;

medical data: electronic medical and health records, results of tests either analytica or subjective, medical diaries, prescriptions etc.;

health data: data relating of the health and well being including sensor data, biometric data, diet tracking, survey answers related to health and quality of life, health diaries, personal data: data relating to an individual's behaviors, habits, and daily activities such as geographic locations visited, purchasing activities, web browsing, friends, social media posts, employee record, academic records, etc. (in general, this may include any or all data relating to an individual, including genomic, health medical, etc.);

familial data: family history including health and medical history, lineage, and genealogy;

environmental data: envirome and exposome data encompasses a) all of the environmental conditions required for successful biological life that affect human health, and b) life-course environmental exposures (including lifestyle factors), from the prenatal period onwards, including quality and chemical, omic, or organic content of air, water, climate, and soil;

genomic data—relating to the make-up of an individual germ-line DNA and data related to somatic mutations including cancer DNA information, typically all cells in an individual's body contain the same genomic data with only minor variations, but not always;

microbiomic data: relating to the nucleotide sequence or taxonomic classification of other organisms that exist symbiotically, parasytically, or commensal with an individual; common locations of these communities are hand, sinuses, mouth, gut, rectum, sex organs, etc.; also included is pathegenomic and viromid data, covering deleterious microbes, fungi, and viruses;

epigenomic data: relating to genomic data that impacts the expression of a person's genome from DNA sequence data to proteins, including for example DNA methylation, histone wrapping, etc.; epigenomic data can be different cell to cell in the body and tissue type to tissue type;

transcriptomic data: the set of all RNA molecules in one cell or a population of cells, often with expression level values included;

proteomic data: a list of proteins occurring within a cell or group of cells, often with relative abundance values;

Pathogenomic data: genomic data and/or phenomic data on pathogens that affect human health; however, studies also exist for plant and animal infecting microbes. These pathogens may include bacteria, viruses, and fungi;

genotype data: relating to determining single nucleotide polymorphisms "SNPs" or single basepair difference between individuals (e.g., A, C, T, G), data sets often including insertions of a single base and deletions of a single base when discussing consumer genomic genotyping data results;

single nucleotide polymorphism data: a variation in a single nucleotide that occurs at a specific position in the genome, often called "SNPs";

short tandem repeat data: a short tandem repeat is a microsatellite, consisting of a unit of two to thirteen nucleotides repeated hundreds of times in a row on the DNA strand;

microsatellite data: a microsatellite is a tract of repetitive DNA in which certain DNA motifs (ranging in length from 1-6 or more base pairs) are repeated, typically 5-50 times;

structural variants: a region of DNA approximately 1 kb and larger in size and can include inversions and balanced translocations or genomic imbalances (insertions and deletions), commonly referred to as copy number variants (CNVs);

haplotype data: a set of DNA variations, or polymorphisms, that tend to be inherited together. A haplotype can refer to a combination of alleles or to a set of single nucleotide polymorphisms (SNPs) found on the same chromosome;

genome methylation data: a list of bases or sets of bases that have been methylated, a process where methyl groups are added to DNA base;

whole or partial gene sequence data: a succession of letters that indicate the order of nucleotides forming alleles within a gene;

whole or partial exome sequence data: a succession of letter that indicate the part of the genome composed of exons, the sequences which, when transcribed, remain within the mature RNA after introns are removed by RNA splicing and contribute to the final protein product encoded by that gene;

whole or partial chromosome data: a succession of letter that indicate the sequence of whole or part of a chromosome;

whole or partial genome sequence data: a succession of letters that indicate the order of nucleotides forming alleles within a DNA (using GACT) or RNA (GACU) molecule;

medical record data: a patient's individual medical record data identifies the patient and contains information regarding the patient's case history at a particular provider; the health record as well as any electronically stored variant of the traditional paper files contain proper identification of the patient;

exercise data: covering any activity, or lack there of, requiring physical effort, carried out especially to sustain or improve health and fitness;

dietary data: pertaining to nutritional status, calories consumed in order to cross-sectionally describe dietary patterns of consumption and food preparation practices, and to identify areas for improvement;

wearable device data: devices that can be worn by a consumer and often include tracking information related to health and fitness; other wearable tech gadgets include devices that have small motion sensors to take photos and sync with your mobile devices;

biometric device data: include any device that tracks biometric data, from heart rate monitors to state-of-the-art ingestible and/or insertable sensors that can provide your granular data about the interworking of your internal systems;

data indicative of at least a portion of the respective member-specific contributed data: some or all of the contributed data may be processed and derived data may be kept, stored, analyzed, etc.; indicative data may include various processed or encoded forms (e.g., tags, structured data, etc.);

structured data or files derived from the received and stored member-specific contributed data: depending upon the processing and analysis, structured data, including tagged data, metadata, etc., may be created based upon raw or partially processed data contributed by members;

Low-pass sequencing: a succession of letters that indicate the order of nucleotides forming alleles within a DNA (using GACT), typically gathered at a sequence redundancy that is not sufficient to assemble an individual's full genome, region of the genome, exome, gene, or chromosome, but is sufficient to identify genotypes or minor structural variants within the genome, gene, chromosome, or exome;

Personally identifiable information: information that can identify the member, either alone or in combination with other information.

Actors member: any person who contributes data that is aggregated and who receives a value for the contributed data;

administrative entity: a company or entity apart from the members and from third party users of the aggregated data, which interfaces with members to receive data used to create member accounts, and receives, processes, and aggregates the contributed data, and then makes the aggregated data available to third parties, such as for research and analysis;

third party: a person or entity apart from the members and from the administrative entity that has an interest in the aggregated data and that interacts with the administrative entity to perform operations on the aggregated data, such as searches and analysis, and who provides remuneration to the member community in cooperation with the administrative entity (third parties may include, for example, pharmaceutical companies, research institutions, universities, medical institutions, governmental and quasi-governmental institutions, and so forth);

successor in interest to the respective member: a person or entity who obtains legal rights to the data of a member (e.g., through an estate);

data users: institution, researchers, foundations, or individuals who search or query the aggregated data;

System Components/Subsystems database: one or more databases, typically maintained by the administrative entity, and containing member data, metadata, data derived from member data, structured data, etc. (databases may be constructed in conventional manners or by specific technologies, such as blockchain);

processing circuitry: one or more digital processors typically embodied in one or more computers, servers, dedicated processing facilities, etc.;

cryptographically encoded ledger: a ledger that is encoded to permit access by cryptographic methods (e.g., based on private and/or public keys);

immutable ledger: a ledger that cannot be changed, or that cannot be changed without the change being evident;

blockchain: a growing list of records, called blocks, which are linked using cryptography; each block contains a cryptographic hash of the previous block, a timestamp, and transaction data; by design, a blockchain is resistant to modification of the data;

account database: a database, typically maintained by the administrative entity that stores member account data, which may include member-identifying data and data related to ownership of databases and/or value attributed to a member;

contributed data database: a databased that contains de-identified and/or encrypted data contributed by members; the data of the contributed data database may be any type of data mentioned above, for example;

account blockchain or distributed ledger protocol: consensus protocol; a process, encoded in software, by which computers in a network, called nodes, reach an agreement about a set of data;

contributed data blockchain or distributed ledger protocol: a protocol that utilizes blockchain and/or distributed ledger technologies for receiving, processing, aggregating and storing contributed data;

universal resource identifier protocol: a Uniform Resource Identifier is a string of characters that unambiguously identifies a particular resource; schemes specifying a concrete syntax and associated protocols define each URI.

data key: a digit or physical key which holds a variable value which can be applied to a string or a text block, in order for it to be encrypted or decrypted;

data key for each member-specific account is stored in an encrypted manner;

one-way pointer: a programming language object that stores the memory address of another value located in computer memory;

secure alternative authentication protocol that maintains a de-identified nature of the stored member-specific contributed data;

secure alternative authentication protocol comprises accessing a contact address for the respective contributing member;

secure sandbox memory: a virtual space in which software can be run securely and logic can be applied to control queries and query responses;

secure cloud service site: a platform of servers, whereas your virtual sites live on multiple computers, eliminating any single point of failure; such sites are secure, and ultra reliable, and generally always online;

educational interface pages: interface pages and materials that may be served to members for educating the members of the workings of the community system, the details and types of data that may be contributed, the details and types of value that may be obtained by joining and participating in the community, as well as to better educate members regarding such things are how to improve data quality, how to maintain accurate and up-to-date data, etc.;

segregated data key: data is separated such that accessing one portion of a record does not automatically allow access to other portions of the record;

segregation data key database: a structured set of data that contains key (a variable values that is applied to a string or block of text to encrypt or decrypt it) that is used to encrypt or decrypt data;

Value-Related Components member-specific accounts: accounts established for individual members that allow for contribution of data, management of member activities, accounting and tracking ownership and/or value attributed to a member, opting in and out of activities, etc.;

member-specific value: value attributed to individual members by virtue of their participation in the community, such as by contribution of data; value may be in one or more forms, including, for example, ownership shares, currency, cryptocurrency, tokens, etc.;

pre-established calculation: mathematical calculation or logic based calculation established and officially implemented prior to usage;

asset amount: an amount of something of value, typically referring to value attributed to members for their participation in the community;

currency: a basis of value, such as money or some other commonly recognized basis of transaction;

cryptocurrency: a digital currency in which encryption techniques are used to regulate the generation of units of currency and verify the transfer of funds;

member-specific value is at least partially based upon the quality evaluation: value may be altered (increased or decreased) based upon a quality, reliability, or similar determination (e.g., of the data, of a source of the data, of the contributor, of past interactions, etc.);

smart code: executable code that provides for defined steps or operations recorded in a verifiable manner (e.g., an immutable ledger);

a smart contract: a computer protocol intended to digitally facilitate, verify, or enforce the negotiation or performance of a contract (e.g., through the use of smart code);

educational module/video: educational materials that may be provided (e.g., served) to members in a desired sequence to systematically lead the members through an instructional program;

third party interface: pages or other materials that may be served to third parties to allow for activities such as the establishment of accounts, requests for studies and searches of aggregated data, conveyance of value (e.g., remuneration) for such activities, and potentially for contacting members for follow-up activities (e.g., clinical studies);

Operations aggregate data: data combined from several measurements and/or inputs; when data are aggregated, groups of observations are replaced with summary statistics based on those observations;

attribute value: to cause value to be created and recognized;

transfer remuneration/currency/value: attributed or record compensation of a defined sort, such as in a member account;

separately store (data of different types): store and/or segregate data in different databases;

de-identifying member data (e.g., contributed data): data that has undergone a process that is used to prevent a person's identity from being connected with information;

the administrative entity does not link member-specific contributed data to an associated member-specific account in a manner that would personally identify the respective contributing member;

sending data to the contact address without accessing the stored member-specific contributed data;

quality evaluation: a process used to determine the accuracy, veracity, and potential value;

quality scoring: applying a function or a look-up table in order to represent the quality of data;

determining inconsistency with member-specific contributed data;

sending a notice to a contributing member of results of the quality evaluation;

generating a report of results of the quality evaluation;

contributor evaluation: analysis of data and/or activities of members contributing data to determine aspects such as reliability that may affect the use of data contributed;

contributor scoring: a number or factor that may be generated based on contributor evaluation and that may be used, for example, in later interactions with the same member (e.g., as more or less "trusted") and/or that may affect a value attributed based upon contributed data;

evaluation of past data submissions: analysis of data, data sources, contributing members, and so forth based upon evaluation of historical interactions and contributions of the member;

evaluation of a third party source: analysis of an entity that generated or processed contributed data, such as to determine data quality, completeness, reliability, etc. (such third parties may include, for example, sequencing facilities, medical facilities, etc.);

processing of later member-specific contributed data is altered for trusted contributing members;

interacting of the respective contributing member with the educational interface pages;

completion of successive educational modules;

compensating contributing members based upon interaction by the respective contributing member with the educational interface pages;

accessing to the aggregated member-specific contributed data without permitting third party identification: activities between the administrative entity and third parties to aid in analysis of aggregated data, such as for research and discovery without relating the aggregated data back to individual contributing members in a way that would identify the members;

remunerating by/from the third party: transfer of value from entities interested in the aggregated data in exchange for activities such as searching, access, etc.;

stages of interaction by the third party third party interface: progressive activities of establishing an account or relationship between the third party and the administrative entity, arranging for remuneration for activities with the aggregated data, etc.;

third party interface is configured to cooperate with the processing circuitry to perform searches;

permitting communication by the third party to contributing members without permitting third party identification: following analysis by a third party, allowing certain contact (e.g., via email) between the third party and contributing members (e.g., for invitation to clinical trials) in a way that does not provide the third party with the actual identification of the contacted members;

third party communicating based upon a unique identifier associated with the aggregated member-specific contributed data of the contributing members: similar communication but based upon technologies where the members are associated with identifiers that do not allow for personal identification of the members;

opting-out of communication by the third party: an operation that a member may perform (e.g., via interface pages) to preclude being contacted by third parties;

attributing a value to at least some of member-specific accounts based upon remuneration provided by the third party for access to the aggregated member-specific contributed data: channeling of value (e.g., remuneration) based upon interest in or use of member data by third parties, typically through the intermediary of the administrative entity;

attributing the value to at least some of the member-specific accounts based upon remuneration provided by the third party;

attributing a value is based upon whether the respective member-specific contributed data corresponds to criteria provided by the third party: may relate to specific remuneration or channeling of value to certain members whose contributed data is of particular interest to a third party;

selecting a portion (for sandbox) of the aggregated member-specific contributed data for access by the third party: down-selecting some data from the aggregated data that meet criteria of a third party, such as resulting from a search;

segregating data: data for a given individual being segregated across several databases to increase security; each database has a different key for the individual so information cannot be combined without having all of the keys for an individual (stored in the segregation key database).

Description of Embodiments

Figure 1:
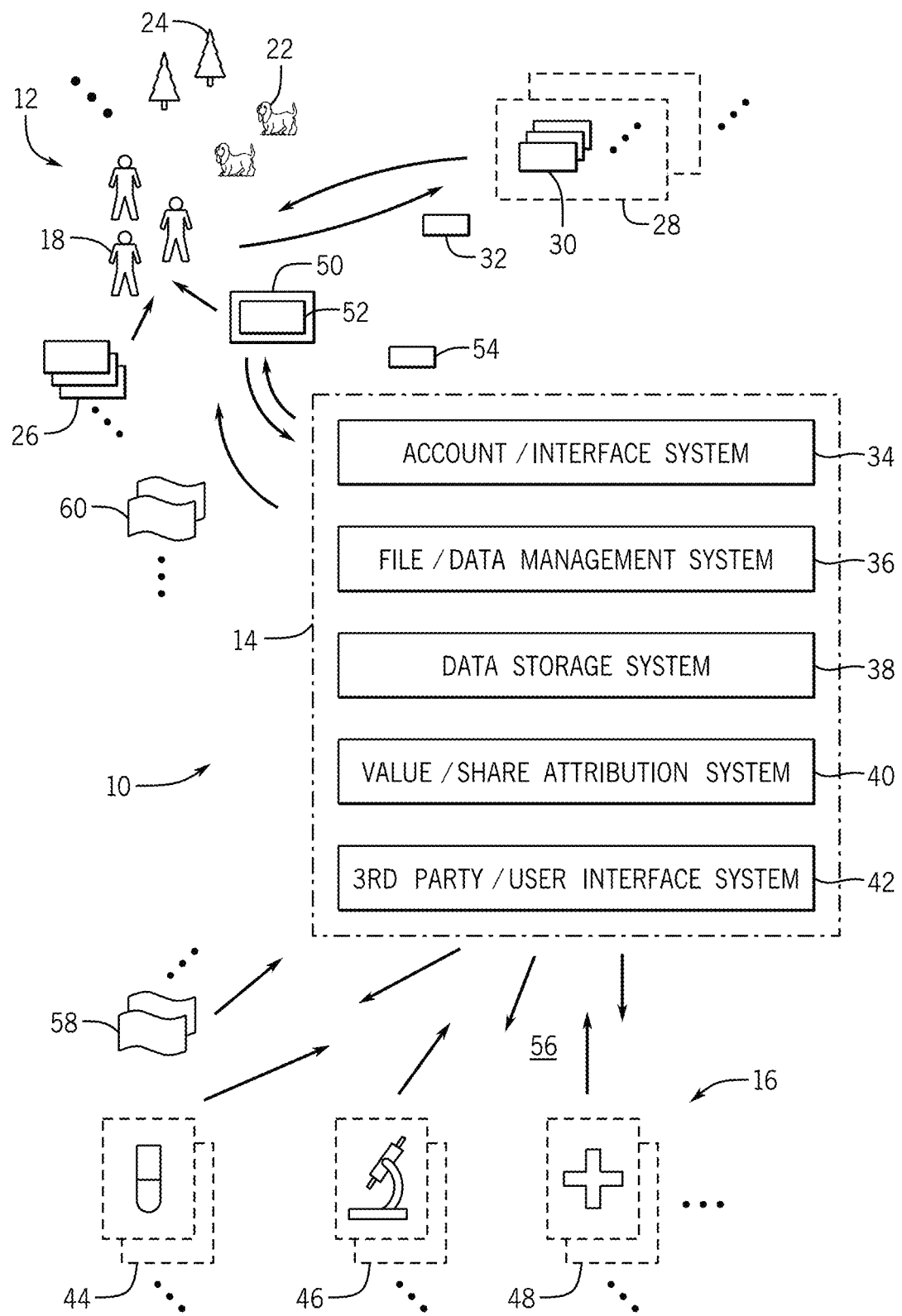
FIG. 1 is a diagrammatical representation of an example genomic and medical data aggregation system.

Turning now to the drawings, FIG. 1 illustrates an example data aggregation and management system 10 at the service of a member population 12. The system includes and is managed by an aggregation administrator or coordinator 14. The member population may be thought of in some respects as "users" 16 (but who are or will become contributing members, as distinguished to third party entities who may be interested in the aggregated data and arrange remuneration for access and "use" as discussed below) to the extent that they will interact with the system via served interfaces both to create accounts, to contribute member-specific contributed data, and to manage aspects of their account and data. They will typically comprise human contributors 18 made up of individual members 18 who may create member accounts and contribute data as set forth in the present disclosure. The populations may also include any type of organism for which members may have data, including, without limitation, animal populations 22, and other populations 24 (e.g., plants, microbes, environmental areas such as water and earth sources).

The system allows for data, files, and records 26, 30 to be accessed, and uploaded for processing and aggregation of their content. In the present disclosure, contributed data may be referred to simply as "data" or "files" or "records" interchangeably. As discussed in the present disclosure, provisions are made for de-identifying the data contributed, that is, for removing the ability to relate the contributed data back to an identity of the contributing member, unless the member desires and consents to such identification. Management of the data, the account, and coordination of value attribution is by the system administering entity (i.e., the aggregation administrator or coordinator).

The contributed data may include genomic, or more generally omic data, medical data, personal data, including personal, family, medical and similar historical data, medical records, and any other data that may be of value in research and/or analysis of physical states or conditions of the relevant populations. These may be in the possession and/or control of the contributing member, as indicated by reference numeral 26, or may be held in trust by various institutions 28, as in the case of files 30. In such cases, the members may access the files by physical or electronic transfer, as indicated by reference numeral 32.

The system provides a number of services, and these may evolve depending upon the organizational structure of the administering entity, and the needs and desires of the member community and third party users. For example, in the illustrated embodiment, these may include an account interface system 34, a file/data management system 36, a data storage system 38, a value/share attribution system 40, and a third party interface system 42.

As discussed above, a wide range of individuals, institutions, businesses, and communities may find the aggregated data valuable, and may be willing to participate in permitted uses under the conditions set forth by the system. For example, it is contemplated that pharmaceutical institutions 44, research institutions 46, as well as various medical, governmental, and other institutions 48 may from time to time subscribe to services that allow for pre-established or customized access and use. It is contemplated that smart contracts may be established to permit and/or to track such activities as searching, analysis, selection of criteria for specialized access or searching, and so forth. As set forth in this disclosure, arrangements are contemplated for remuneration of such activities, with value flowing back to the community members as exchange for their participation in making the data contribution.

In the illustrated embodiment, the members will interface with the system via a computer 50 (or any other capable device, such as a tablet, smart phone, etc.). Data exchange 52 will be enabled by any desired network connection, so that member data, account data, and contributed data/files 54 may be provided. Similarly, data exchange 56 will take place, also by any desired network connections, with the third party users. Ultimately, based upon the arrangements with these users, value 58 will flow back to the administrating entity 14 and therethrough to the member community, as indicated by reference 60. Many forms of value may be provided, including monetary payments, cryptocurrency payments, ownership shares, and so forth.

As noted in the present disclosure, in some currently contemplated embodiments, interactions between the community members and the administrating entity may or may not be based upon smart contracts, as are interactions with the third party users. Moreover, the ownership and value attributed to the community members may be based upon one or more encrypted, decentralized, and/or public ledgers, cryptocurrencies, and so forth. Such techniques may allow for reliable tracking and "transparency" in transactions, while the present techniques nevertheless are based on confidentiality and member control of personalized or identity-permitting data and data associations.

Figure 2:
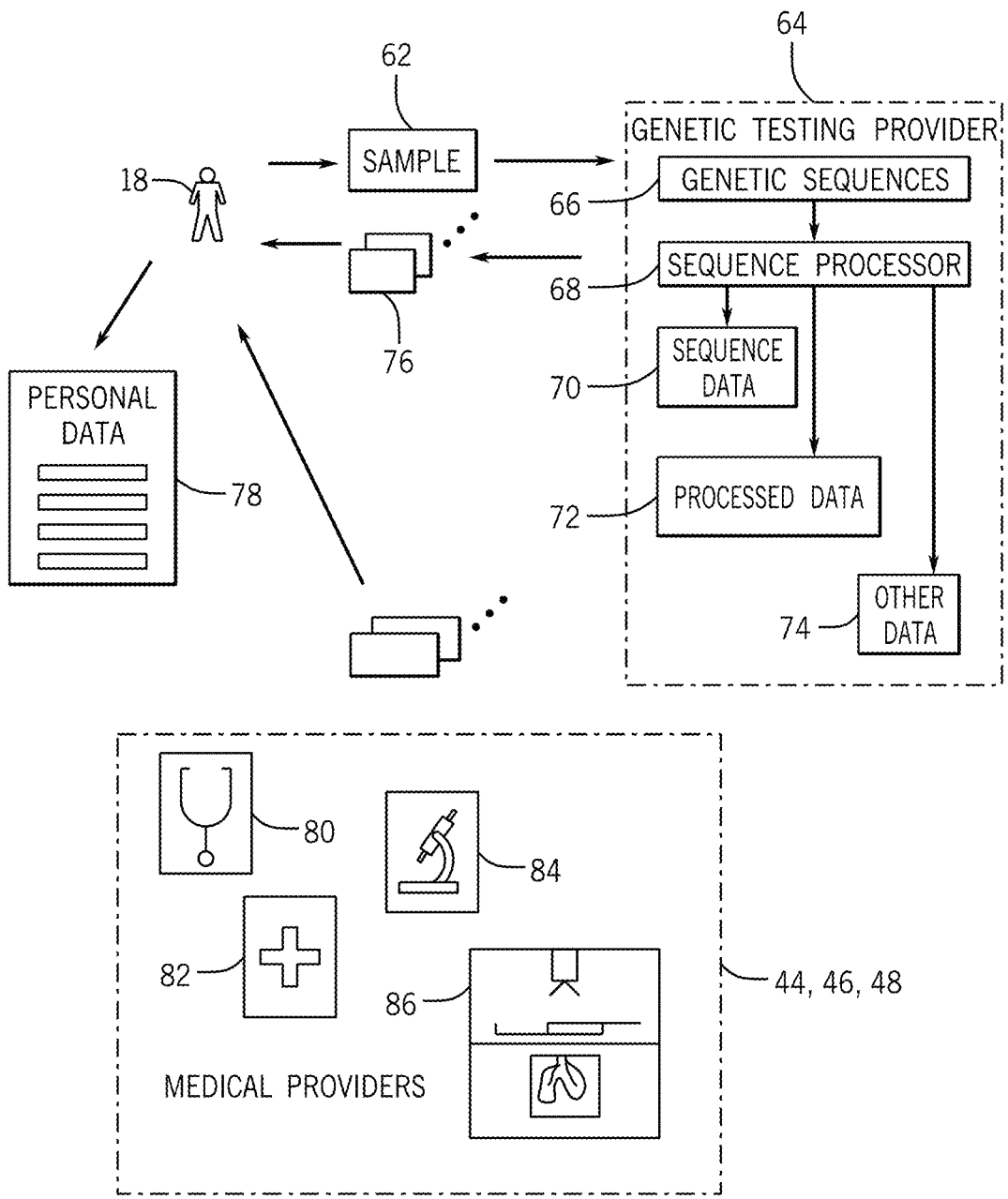
FIG. 2 is a diagrammatical representation of example data and file originating processes.

FIG. 2 illustrates certain of the types of data and data exchange that may be envisaged for the system. As discussed above, the system is based upon contributions by human contributors 18. For genetic and other similar types of data, these may be based upon a sample 62 taken from the individual or from any other population accessible to the individual, such as animals, microbes, plants, environments, and so forth. Such samples may be provided to a genetic testing provider 64. In accordance with known technologies, a genetic sequencer 66 may analyze genetic and other biological materials by DNA sequencing. Based upon such sequence data, the sequencer may forward the data to a sequence processor or processing system 68 where individual strands of sequenced information are pieced together to form larger segments, and in certain cases segments representing entire genes, chromosomes, extra chromosomal DNA, RNA, and other biological material of interest. The resulting aligned sequence data 70 is typically stored in one or more files. Other processed data 72 may be available based upon the sequence data, such as identification of individual genes, gene variants, and so forth. Finally, such providers may carry out further processing to acquire various other types of data as indicated by reference 74. All or part of the data is typically provided back to the individual in the form of one or more files 76.

In other contexts, personal data 78 may be provided by the individual. Such member-specific data may include, for example, identification of the individual or source of the data (e.g., animal, plant, microbe, environment, sub-population, etc.). In certain contexts, the administrating entity may provide queries, forms, questionnaires, surveys, wearable data and so forth that may be completed by the member on-line or off-line for processing and aggregation.

Further, institutions 44, 46, 48 may derive data from medical visits, local environmental data, medical procedures, personal interfacing, and so forth with the member community. In the embodiment illustrated in FIG. 2, for example, medical facilities and physicians 80 will typically keep on ongoing electronic medical records, as may hospitals 82. Certain research facilities, such as universities, pharmaceutical companies, and so forth as indicated by reference 84 may obtain and keep other information on the individual or population. Still further, laboratories and imaging facilities as indicated by reference 86 may have further information including, image information, structured data derived from image information, and so forth. All of these may be further provided in the form of files that can be transmitted to the member as indicated in FIG. 2.

FIG. 3 diagrammatically illustrates an example of account initiation and member interaction processes in accordance with certain presently contemplated embodiments. The process may begin with the member 18 interacting with a personal computer 90, or other device that can interact with the internet. Interface screens 92 are served to the member computer by a member portal 94 maintained or overseen by the administrative entity of the system. The member portal itself may run on any suitable type of computer or combination of computers and will be in communication with the member computer by the Internet or any suitable network or combination of networks. The member may contact the portal by a conventional URL, or by a browser search, or any other initial contact mechanism. The interface screens will walk the member through the account creation and data transfer process. As will be appreciated by those skilled in the art, the computer system running the member portal will typically comprise one or more interfaces 102 designed to allow for data exchange between the administrative entity site and the user computer. The interface 102 is in communication with one or more processors 104 and memory 106. The memory may store the interface screens, routines for generating the interface screens, routines for processing member data, and so forth, these routines being executed by the processor. The member portal 94 is in communication with and executed based upon a member API 96.

Similarly, an account portal 98 is provided for interacting with the member computer in ways relating to the member account. The account portal may communicate again by any suitable network or combination of networks, and may operate based upon, among other things, a shares API 100. As noted below, various approaches, protocols, and processes may be implemented to generate and account for value or shares in the database or databases of the present system. The account portal computer or computers may include one or more interfaces 108 designed to permit interaction with the member computer as well as one or more processors 110 and memory 112. Here again, the memory will typically store various screens and interaction protocols that are implemented by the processor via the interface.

As noted above, interaction with the administrative entity may be based upon one or more smart contracts as indicated by reference 114 in FIG. 3. Such smart contracts may detail and/or manage various interactions, stages of interactions, responses to interactions, and may keep reliable and traceable records of interactions with the members. In presently contemplated embodiments these interactions will be noted on ledger entries as indicated by reference 116 in FIG. 3. As also shown in FIG. 3, data storage devices or systems 118 and 120 are provided for member data and for shares data, and these may be maintained through various processes as discussed in greater detail below.

FIG. 4. illustrates certain example operations that may be considered in processing via the components of FIG. 3. The process of account creation, indicated generally by reference 124 may begin with a prospective member accessing an online tool as noted at operation 126. This online tool may take the form of a screen or screens that permit input of data and provide directions and information to the perspective member. At operation 128, then, the prospective member creates an account and this account may be verified, such as by verifying an email contact for the member. At operation 130, then, a unique member ID is created. Importantly, this member ID may be used for all member interactions with the system, and is a part of the basis for separating individual or personal data from the data uploaded for aggregation. That is, respecting member anonymity or confidentiality, the unique ID allows for many types of member interaction with the system while maintaining separation between the aggregated data or files and the personal identification of the member. The member idea may be encrypted locally on the member computer using member login information, such that it is not directly linked to the member's account until it is unencrypted.

At operation 132, then, any information provided by the new member is stored, and at operation 134 identifying information is separately stored. It may be noted that through all of these operations, and based upon the protocols set forth in the smart contract, quality control and other required operations or milestones may be performed as indicated by block 136. For example, when data is uploaded the smart contract may call for a quality control operation on the data and a response may be defined, such as receiving a quality control metric, as well as an action may be taken, such as to compare the metric to a pass/fail hurdle, to make a pass or fail decision, and so forth. Responses may also be defined at such steps, such as indicating to the user whether data is acceptable or not, whether data or files pass or fail, and, for example, if the response is a "pass" the data may be entered into the database, shares in the database may be allocated, entries may be made to a ledger, and so forth as described below. Similarly, in the case of a "fail", actions may include placing data into a failed data queue, informing the user, making a leger entry, and so forth.

The information provided by the member may be stored as indicated generally by reference 136. Processes presently contemplated for storing such data and files are described more fully below. It is also contemplated that the member may have direct access to certain data and files, and in such cases, may upload the data or files directly. In other cases, the member may instead provide links to data and files that can be the basis for access by the processing systems of the administrative entity. In yet other cases the members may fill out a survey and the data would be extracted from the answers directly or after quality control testing and other processing.

FIG. 5 illustrates example processes presently contemplated for uploading, receiving and processing member data files. The processes may begin with the uploading of data or files as indicated at block 138 (continuing from FIG. 4 above). As noted above, all search processes may be performed in accordance with protocols established by one or more smart contracts as indicated at 114 in FIG. 5. Each stage executed may include initiating actions, receiving responses, and taking actions based upon received responses. For each of these steps or stages in execution of the smart contract, and based upon the interactions between the system and the member, ledger entries are made as indicated at reference 116 to maintain a reliable record of the interactions. Though not separately illustrated in FIG. 5, such smart contract stages and ledger entries are made or may be made at all of the various steps of processing.

The uploading process transfers data or a file 140 to one or more temporary storage systems 142. Temporary content storage, as indicated more generally by reference 144 may store unprocessed or partially processed data or files waiting in a queue for other actions, such as quality control. Individual files 146 are then transferred by a quality control broker 148 for one or more types of quality control. In certain presently contemplated embodiments, structured data or files may be converted or processed to make them more understandable, comparable, or to facilitate extraction of data for aggregation. Such files, as indicated by reference 152, may be transferred to a converter cluster 150. Genomic data files, for example, may be most useful when placed into a structured and standard format. Converter cluster 150 may provide processing for creating congruent files, verifying that the files relate to a particular population, species, individual, and so forth, for formatting the files and contents of the files and so forth. Where such processing or conversion is not desired or required, the files may be passed to a quality control process content storage 154 as indicated by reference 156, or the converted or processed files may be similarly placed in the quality control process content storage as indicated by reference 158 in the figure.

Files waiting in a queue in the quality control process content storage may be individually transferred, then, as indicated at 162 by a quality control broker 160 to perform validation on the files. The files sent for validation, indicated at reference 166 are considered by a validation cluster 164. Validation of data or content of such files may be performed based upon the type of data in the file, expected aspects of the data, standard data to which the processed data may compared, and so forth. For example, the validation cluster may check for redundancy or near redundancy (e.g., a member has uploaded the same data more than once, or copied a file and has made one or few changes, commonality of variants (e.g., the member has uploaded inconsistent files), verifications versus reference data (e.g., genomic data compared to human or other species reference genomic data), statistical analysis of the data, and so forth. The validation cluster may produce a validation or analysis report as indicated by reference 168. Thereafter, the validated or processed files 172 may be transferred to a validated data storage 170.

Individual files may then be extracted from the validated data storage as indicated by reference 176 to a quality/credibility analyzer 174. In particular, various types of quality and credibility, or more generally reliability, may be measured and scores may be attributed that may be used for various purposes, including, where desired, attribution of shares or value. For example, a credibility score or report may be generated at operation 178. Based upon such scores, certain members may be designated as "trusted" or reliable members, and later processing of contributions by such members may be altered, such as by alteration of certain quality control applied to the data or files, or value attributed to the data or files based upon the quality and/or reliability of the underlying data. The credibility score may be saved and be used later as part of a statistical analysis evaluating the overall credibility of all the data provided, by a machine learning protocol, or by a user for the statistical confidence of conclusions in a study across multiple users. At operation 180, the analyzer may also determine that the processing of the data is successful or that a failure has occurred, requiring either sequestration of the data, partial acceptance of the data and so forth. At operation 182, then, value, ownership increment, profit distribution, or shares may be attributed to the member based upon the data. Any suitable formula for attributing value may be applied at this stage, and different formulas may be developed as different types of data and data of interest are determined and provided by members. Examples of calculations for shares or value attribution are discussed above.

Finally, as indicated at references 184 and 186, the data and files are stored. In presently contemplated embodiments, these are stored in separate storage spaces, with genetic files being stored in a first storage space 188 and medical and similar data and files being stored in a storage space 190. Of course, each of these storage spaces may comprise one or many different physical storage media and locations. As noted above for all of the steps and based upon the smart contract protocol implemented, ledger entries are made as indicated at reference 192, and notice is provided to the members of the processing and value attribution as indicated by reference 194.

FIG. 6 illustrates exemplary logic for providing transparent confidentiality in processing of member data and files. As noted throughout the present disclosure, an important aspect of the system is the ability to reliably trace interactions with the system, and between members and the system, as well as third parties in the system. Such interactions should not only be transparent and reliably traceable, but should also respect the confidentiality of the participants, and particularly of the community members. Various processed may be envisaged and implemented to provide both the desired tracing and transparency needed for reliability, as well as member confidentiality. In general, this is done by separation of member identifying data from uploaded data in files. The latter becomes de-identified data which cannot ordinarily be associated with the identity of the contributing member. Nevertheless, the system allows for the account to be created, augmented, and for value (e.g., remuneration) to be passed along to the particular members based upon third party utilization of the database or databases.

In the implementation illustrated in FIG. 6, this process again begins with the uploading of data or files as indicated by reference 138. When the data is uploaded it is stored as indicated by reference 196 and as discussed above. The data may typically be stored at a structured data location as indicated by 198. Moreover, this process again begins a protocol in accordance with smart contract processing as indicated by reference 200. Though not separately illustrated in FIG. 6, it should be borne in mind that this smart contract processing may include individual stages or toll gates that are passed, and each may be associated with actions, responses, notifications, and so forth, all of which are recorded in one or more ledgers.

At block 202, the processing invokes a universal resource identifier protocol (URI). Such protocols may be crafted to provide restricted processing of the data stored at location 198. For example, in a presently contemplated embodiment, the URI protocol will require credentials which may be embedded into queries made by the administrative entity. Accordingly, such queries may be the basis for the processing performed by the administrative entity, and because it is exceedingly unlikely that such credentials could be reproduced by other entities, the URI protocol ensures that only such queries will meet the requirements for response. Moreover, in the presently contemplated embodiment illustrated, a limited number of uses may be made of the data in accordance with the URI protocol as indicated by reference 206. In this contemplated embodiment, a single use is permitted. Further, in accordance with this embodiment, a restriction on the duration or lifetime of the availability of the data or URI is made as indicated by reference 208. Once this time expires, the queries are no longer permitted and the process must move to an earlier stage, possibly including re-uploading of the data.

The figure also illustrates the separation of subsequent operations. For example, based upon processing, and as discussed above, data and files are stored as indicated by reference 210. In a separated way, however, user accessible data is updated as indicated by reference 212. That is, the user account information, value or shares attributed to the user, and so forth may be accessible to the user, while the same information is not accessible to the administrative entity, owing to the separation of the data and files stored at block 210 from the user information accessible at block 212. As indicated at 214, however, the user identity and uploaded data, files, and share information may be linked so that attribution may be made, and remuneration passed along to the members based upon the uploaded data and files, and their utilization by third parties.

As noted above, various approaches and formulas may be used for the attribution or allocation of shares or value based upon the data and files provided by members. FIG. 7 illustrates an exemplary process 216 for such value or share attribution. The process may begin at step 218 where the system evaluates the type of data provided by the member, such as medical data, history data, genomic data (or more generally, omic data), species to which the data is related, and so forth as indicated at reference 220. The system may then perform analysis and quality control on the data as noted above, and as indicated generally by reference 222. The quality of the data may be evaluated at block 224, and the reliability or credibility of the data may be evaluated at block 226. As indicated at block 228, many other factors may be considered that can be incorporated into complex computation of shares or value for individual members and for individual data. In general, the sum of all value attributed to the individual member can be applied regardless of the number of times the data is added, altered, supplemented, removed, and so forth. Based upon factors such as the completeness, quality, reliability, veracity, and so forth, then, the shares calculations discussed above may be applied as indicated at block 230. As always in these processes, where smart contracts are utilized, a ledger entry may be made as indicated at block 232, and the member may be notified at block 234.

As noted above, various formulae, processed, and schemes may be used to attribute shares and value in the one or more databases established for the aggregated data, and for remunerating the member community for contributions as the data is used by third parties. In some presently contemplated embodiments, such allocations of shares may be based on a table of the type illustrated in FIG. 8. This share table 236 provides different numbers of shares for different types of data, as indicated by reference 238, and may impose minimums, maximums, and rates for allocation of shares. In this example, a number of shares may be allocated for an initial data file, as indicated by column 240, for each type of data. Extra or further submissions may be allowed at the initial file value, and these may be limited or restricted, such as for a period of time, as indicated by column 242. Further, additional files of the same type may be permitted, or may be restricted, as indicated by column 246. The table further shows a column for a subtotal of additional shares permitted, as well as a maximum possible shares, as indicated by columns 248 and 250, respectively.

As also discussed above, formulae for allocating shares or attributing value in the one or more databases may comprise a number of factors that may be added to one another or combined in any suitable manner. These may be conditioned (e.g., via a coefficient) based upon the analysis discussed above, such as for data type, source, species, completeness, quality, reliability, and so forth. In practice, quality or reliability scores may also be based on the known or determined quality of sequencing of omic data, the entity that carried out the sequencing or subsequent processing, and so forth.

FIGS. 9A-9J illustrate certain example interface screens that may be used for interacting with prospective and existing members. These may prompt the community to provide useful identifying information, establish accounts, upload information and files, and so forth. They may also provide informative text, images, video, audio, and so forth.

In some embodiments, established protocols may allow for members to access information (e.g., videos) or to interact with each other anonymously that better inform the members or that enhance member participation or quality of the data. These may be defined by smart contracts as well.

As noted in the present disclosure, smart contracts (e.g., via public ledgers, encrypted ledgers, distributed ledgers, "blockchain" technologies, etc.) may be used at various stages in the interactions between the community members and the administrative entity, as well as with third party users of the aggregated data. In the present context, such techniques may address the need for transparency of data use, accuracy of information, managing and/or tracking of complex transactions, removal of central control of operational details while supporting mechanisms for anonymity of the data owners (members), mechanisms for associating value exchange for contribution and use of data, and for connections between "on-" and "off-chain" data.

In presently contemplated embodiments, not all information is stored on the blockchain or distributed ledger for a variety of technical, regulatory, and security reasons. All information is stored encrypted at rest and is encrypted in transit. Genomic, clinical, and Personal Health Information (PHI) data are segregated and stored with independent unique keys hashed based on the same unique identifier. The independent hashed keys are decrypted in flight by a centralized tokenization service and joined together in a separate secure database that contains hashed passwords, user ID, and the like. Segregation is used to make each of the independent data sources resilient to being compromised; multiple data sources must be compromised before any utility can be recovered from the data.

In particular, as noted above, when a member creates an account certain data is exchanged, and in particular, the member may create their digital credentials and explicitly accept an informed consent for population level research. They can opt-out of recontact to ensure that they do not learn something about their genetics that could be alarming. The creation of a user identity is performed anonymously via the ledger with an identity that the system hashes to their administrative data. Next, as summarized above, the user is prompted to add data, and when it is supplied, another transaction is posted that a smart contract executes the appropriate transfer of value, and the data passes through QC and is added to the summary databases, as also summarized above. Here again, the data may be split in a manner that reduces the utility, or ability to re-identify, of each component should a breach ever occur—there are no shared identifiers across these databases.

A third party user also requires digital credentials to access the system. To search the data at a population level a transaction is posted that is attributed to the data user's organization while the query specifics and the list of member IDs remain confidential to the data user. The smart contract extracts the required value for the search before the list of IDs is returned into a secure sandbox for subsequent analysis. Member data is required to remain in the system so that it cannot be disseminated, only statistical data or metadata is allowed to leave the system.

If the user wants to retrieve more information from the genomic or clinical data they issue a second transaction that is posted and attributed to the data user's organization along with the list/cohort for which the data is requested. PHI data cannot be retrieved. As before, the smart contract extracts the required value, and the data set is transferred to the secure sandbox. Subsequent tools can be applied within the sandbox to glean the necessary information sought from the population level data. Additionally tools can be applied in the sandbox to ensure insufficient data is transferred related to a single member in order to eliminate the possibility of re-identification. In the event the third party user would like to follow up with contacts to members (e.g., based upon individual member data of interest, groups of members of interest, drug trials, etc.), such contacts may be driven by a list of member IDs in the sandbox. A description of the request may be provided, along with an invitation to a study. Any compensation being offered will also typically be indicated. A contact (e.g., an email) may be sent with the attribution of the data user's organization and a description of the proposed study and compensation involved. The member may then, at their sole discretion, opt to ignore the request (and remain anonymous) or respond to participate.

It may be noted, as well, that the administrative entity itself may determine reasons to reach out to contributing members in ways that may benefit the members. However, due to the consistent need and desire to avoid identification of the members (and the de-identified nature of the contributed data once received, processed and stored), presently contemplated embodiments may allow for the administrative entity to contact the members, such as by secure and confidential email contact. Such contacts may be made, for example, to assist in filling gaps in contributed data, notifying members of products, possible programs, treatments, clinical trials, platform enhancements, and so forth. In all cases such contacts by the administrative entity would be performed in a "blind" way in which the members contacted are not identified to the administrative entity. Techniques for such contacts may include those discussed above, such as URI technologies, smart contracts, and so forth.

An added benefit of such de-identified or blind contacting of the members by the administrative entity may be compliance with any existing governmental, regulatory, or industry restrictions on identifying the members, including important individual and patient privacy concerns. Due to the ability to securely separate the member-identifying data (e.g., associated with the member account) and member-specific contributed data, such contacts may be made while respecting the anonymity and privacy of the members. As always, membership in the contributing community is predicated on maintaining member privacy, ownership and control. Indeed, the contemplated embodiments include the ability to, here again, allow members to opt out of any such administrative entity contact.

As also mentioned above, members may withdraw from the system, and may delete or remove data contributed. When a data deletion is requested smart contract may extract the value, or shares, from the user that was originally transferred. This data is deleted from the database or databases and from any sandbox using that data. A similar process is invoked when a user wants to delete themselves entirely from the databases (and sandboxes). In presently contemplated embodiments, the preference by the data owner to allow or prevent recontact is established in their user profile at any time, and no value is transferred for this change.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system comprising:
a server including a processor and memory that cooperate to execute stored instructions to, in operation, serve interface pages to contributing members of an aggregation community for receipt of member-specific account data and member-specific contributed data, the member-specific contributed data comprising omic and/or phenotype data submitted by each contributing member or data derived therefrom;
processing circuitry that, in operation, executes stored instructions to interact with data received via the server;
an account database that, in operation, cooperates with the processing circuitry to receive and store member-specific account data based upon interaction of a contributing members; and
a second database that, in operation, cooperates with the processing circuitry to receive and store member-specific contributed data submitted by each member, and aggregates the member-specific contributed data with member-specific contributed data contributed by other contributing members, at least part of the member-specific contributed data being transformed from a form received from contributing members to a structured and standard format prior to storage in the second database and the aggregation is performed on the structured and standard format member-specific contributed data;
wherein the processing circuitry, in operation, executes stored instructions to process the received and stored member-specific contributed data and perform a quality evaluation of the received and stored member-specific contributed data; wherein the quality evaluation assesses reliability or credibility of a contributing member and/or evaluation of quality of data submitted by the contributing member;
wherein the stored and aggregated member-specific contributed data is de-identified from the stored member-specific account data via encrypted data keys; and
wherein a value is attributed to each contributing member based upon the contribution of the member's member-specific contributed data, the value comprising a share interest in an entity associated with regulation of access to the aggregated member-specific contributed data, and the attributed value is entered by the entity in the member-specific account data while maintaining keyed separation of the member-specific account data from the member-specific contributed data to preclude the entity from personally identifying the member-specific contributed data based on the share interest, and wherein the value is attributed to each contributing member based upon the quality evaluation of the member's member-specific contributed data.

2. The system of claim 1, wherein transactions with the account database and with the second database are recorded in a distributed immutable ledger, including the attribution of the value as a share interest.

3. The system of claim 2, wherein the system permits third parties to interact with the aggregated member-specific data, and transactions of the third parties with the aggregated member-specific data are recorded in the distributed immutable ledger.

4. The system of claim 3, wherein as the member-specific contributed data is received and stored, ledger entries are made separately to the distributed immutable ledger.

5. The system of claim 3, wherein the processing circuitry invokes a universal resource identifier protocol to process the member-specific contributed data.

6. The system of claim 1, wherein each member-specific account is associated with a data key.

7. The system of claim 6, wherein the data key for each member-specific account is stored in an encrypted manner on a distributed immutable ledger with a one-way pointer from personal information indicative of the member-specific account to a respective data key.

8. The system of claim 6, wherein the second database stores member-specific contributed data of different types, including at least omic data and health data, and wherein at least two data types are associated with a different respective data keys.

9. The system of claim 1, wherein the second database is maintained by an administrative entity that allows analysis of the aggregated member-specific contributed data, and wherein the administrative entity does not link member-specific contributed data to an associated member-specific account in a manner that would personally identify a respective contributing member without permission of the respective contributing member.

10. The system of claim 1, comprising separate portals for receiving the member-specific account data and the member-specific contributed data.

11. A system comprising:
a server including a processor and memory that cooperate to execute stored instructions to, in operation, serve interface pages to contributing members of an aggregation community for receipt of member-specific account data and member-specific contributed data, the member-specific contributed data comprising omic and/or phenotype data submitted by each contributing member or data derived therefrom;
processing circuitry that, in operation, executes stored instructions to interact with data received via the server to receive and process the member-specific account data and the member-specific contributed data, and to perform at least one quality evaluation on the member-specific contributed data, wherein the at least one quality evaluation assesses reliability or credibility of a contributing member and/or evaluation of quality of data submitted by the contributing member;
an account database that, in operation, cooperates with the processing circuitry to receive and store member-specific account data based upon interaction of a contributing members; and
a second database that, in operation, cooperates with the processing circuitry to receive and store member-specific contributed data submitted by each member, and aggregates the member-specific contributed data with member-specific contributed data contributed by other contributing members, at least part of the member-specific contributed data being transformed from a form received from contributing members to a structured and standard format prior to storage in the second database and the aggregation is performed on the structured and standard format member-specific contributed data;
wherein the stored and aggregated member-specific contributed data is de-identified from the stored member-specific account data via encrypted data keys; and
wherein a value is attributed to each contributing member based upon the contribution of the member's member-specific contributed data, the value comprising a share interest in an entity associated with regulation of access to the aggregated member-specific contributed data, and wherein the value is attributed to each contributing member based upon the at least one quality evaluation of the member's member-specific contributed data; and and wherein transactions with the account database and with the second database are recorded in a distributed immutable ledger, including the attribution of the value as a share interest, and the attributed value is entered by the entity in the member-specific account data while maintaining keyed separation of the member-specific account data from the member-specific contributed data to preclude the entity from personally identifying the member-specific contributed data based on the share interest.

12. The system of claim 11, wherein the processing circuitry is configured to attribute the value in the member-specific account data based at least in part upon access to the member-specific contributed data by a third party.

13. The system of claim 11, wherein the processing circuitry is configured to assign a quality score to the member-specific contributed data based upon the at least one quality evaluation.

14. The system of claim 11, wherein the second database is maintained by an administrative entity that allows analysis of the aggregated member-specific contributed data by third parties, and wherein the administrative entity does not link member-specific contributed data to an associated member-specific account in a manner that would personally identify a respective contributing member to the third parties without permission of the respective contributing member; and transactions of the third parties with the aggregated member-specific data are recorded in the distributed immutable ledger.

15. The system of claim 14, wherein a value is attributed to the member-specific account data based upon access by the third parties to the member-specific contributed data, and wherein transactions attributing the value are stored in the distributed immutable ledger.

16. A system comprising:
a server including a processor and memory that cooperate to execute stored instructions to, in operation, serve interface pages to contributing members of an aggregation community for receipt of member-specific account data and member-specific contributed data, the member-specific contributed data comprising omic and/or phenotype data submitted by each contributing member or data derived therefrom;
processing circuitry that, in operation, executes stored instructions to interact with data received via the server to receive and process the member-specific account data and the member-specific contributed data, and to perform at least one quality evaluation on the member-specific contributed data, and that attributes a value in the member-specific account data based upon the member-specific contributed data and the at least one quality evaluation, wherein the at least one quality evaluation assesses provenance, or credibility of a contributing member and/or evaluation of a source of data submitted by the contributing member;
an account database that, in operation, cooperates with the processing circuitry to receive and store member-specific account data based upon interaction of a contributing members; and
a second database that, in operation, cooperates with the processing circuitry to receive and store member-specific contributed data submitted by each member, and aggregates the member-specific contributed data with member-specific contributed data contributed by other contributing members, at least part of the member-specific contributed data being transformed from a form received from contributing members to a structured and standard format prior to storage in the second database and the aggregation is performed on the structured and standard format member-specific contributed data;
wherein the stored and aggregated member-specific contributed data is de-identified from the stored member-specific account data wherein the stored and aggregated member-specific contributed data is de-identified from the stored member-specific account data via encrypted data keys; and
wherein the value comprises a share interest in an entity associated with regulation of access to the aggregated member-specific contributed data, and the attributed value is entered by the entity in the member-specific account data while maintaining keyed separation of the member-specific account data from the member-specific contributed data to preclude the entity from personally identifying the member-specific contributed data based on the share interest, and wherein the value is attributed to each contributing member based upon the at least one quality evaluation of the member's member-specific contributed data.

17. The system of claim 16, wherein each member-specific account is associated with a data key.

18. The system of claim 17, wherein the data key for each member-specific account is stored in an encrypted manner on a distributed immutable ledger with a one-way pointer from personal information indicative of the member-specific account to a respective data key.

19. The system of claim 16, wherein the value represents a share interest in an entity associated with regulation of access to the aggregated member-specific contributed data.

* * * * *